(12) United States Patent
Löffler et al.

(10) Patent No.: US 11,772,063 B2
(45) Date of Patent: Oct. 3, 2023

(54) METHOD AND DEVICE FOR PRODUCING SACCHARIDES AND SACCHARIDE ARRAYS

(71) Applicant: Max-Planck-Gesellschaft zur Förderung der Wissenschaften e.V., Munich (DE)

(72) Inventors: Felix Löffler, Potsdam (DE); Marco Mende, Potsdam (DE); Stephan Eickelmann, Potsdam (DE); Peter H. Seeberger, Kleinmachnow (DE); Alexandra Tsouka, Berlin (DE); Jasmin Heidepriem, Rathenow (DE); Grigori Paris, Berlin (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 319 days.

(21) Appl. No.: 17/414,965

(22) PCT Filed: Dec. 17, 2019

(86) PCT No.: PCT/EP2019/085806
§ 371 (c)(1),
(2) Date: Jun. 17, 2021

(87) PCT Pub. No.: WO2020/127391
PCT Pub. Date: Jun. 25, 2020

(65) Prior Publication Data
US 2022/0062849 A1    Mar. 3, 2022

(30) Foreign Application Priority Data

Dec. 18, 2018 (EP) ..................................... 18213784

(51) Int. Cl.
*C07H 1/00* (2006.01)
*B01J 19/00* (2006.01)

(52) U.S. Cl.
CPC ............ *B01J 19/0046* (2013.01); *C07H 1/00* (2013.01); *B01J 2219/00495* (2013.01); *B01J 2219/00596* (2013.01); *B01J 2219/00659* (2013.01); *B01J 2219/00675* (2013.01); *B01J 2219/00731* (2013.01)

(58) Field of Classification Search
None
See application file for complete search history.

(56) References Cited

U.S. PATENT DOCUMENTS

2011/0313148 A1    12/2011    Christ et al.

OTHER PUBLICATIONS

International Search Report and Written Opinion for International Patent Application No. PCT/EP2019/085806 dated Apr. 9, 2020, 11 pages.
Monzo et al., Immobilization Techniques for Mono- and Oligosaccharide Microarrays, Accepted: May 15, 2006, 6 pages.
Plante et al., Automated Solid-Phase Synthesis of Oligosaccharides, Feb. 23, 2001, 5 pages.

*Primary Examiner* — Christopher M Gross
(74) *Attorney, Agent, or Firm* — AMIN, TUROCY & WATSON, LLP

(57) ABSTRACT

The present invention relates to a method and a device for producing saccharides and saccharide arrays. Said method is particularly useful for the synthesis of saccharides in parallel and of high-density saccharide arrays, such as microarrays, which are required for high-throughput screenings.

15 Claims, 14 Drawing Sheets

Figure 4

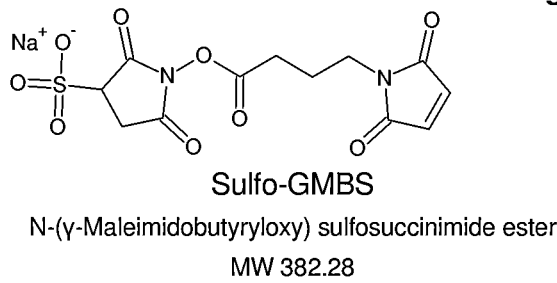

Sulfo-GMBS
N-(γ-Maleimidobutyryloxy) sulfosuccinimide ester
MW 382.28
Spacer Arm 7.3 Å

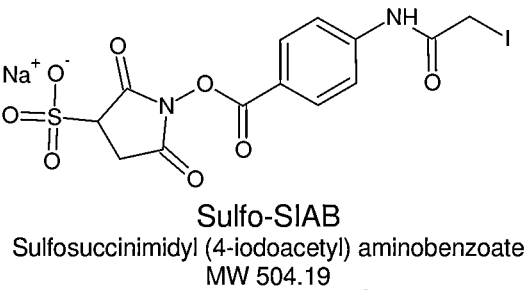

Sulfo-SIAB
Sulfosuccinimidyl (4-iodoacetyl) aminobenzoate
MW 504.19
Spacer Arm 10.6 Å

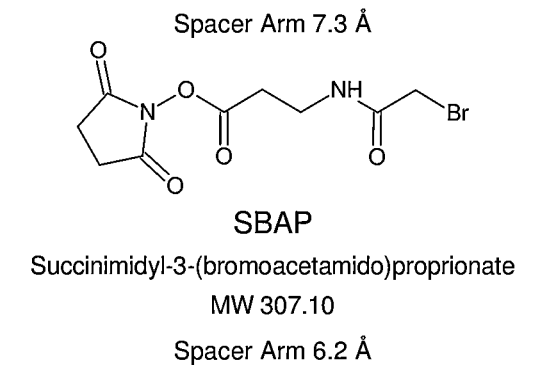

SBAP
Succinimidyl-3-(bromoacetamido)proprionate
MW 307.10
Spacer Arm 6.2 Å

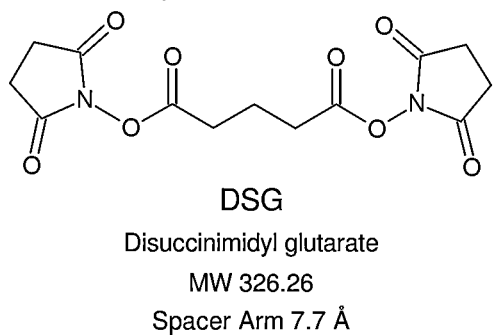

DSG
Disuccinimidyl glutarate
MW 326.26
Spacer Arm 7.7 Å

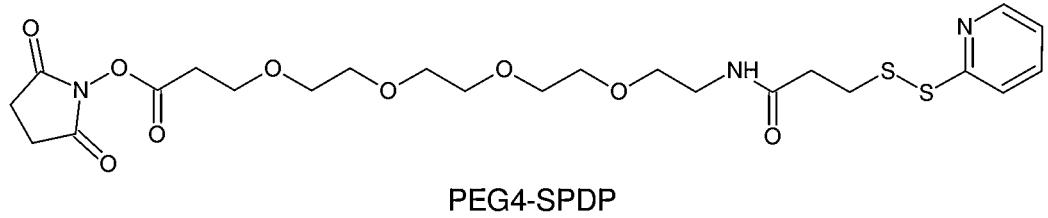

PEG4-SPDP
2-Pyridyldithiol-tetraoxatetradecane-N-hydrosuccinimide
MW 559.17
Spacer Arm 25.7 Å

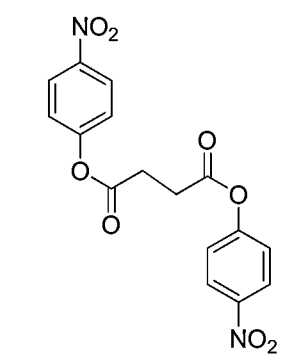

Bis-(4-nitrophenyl)succinate

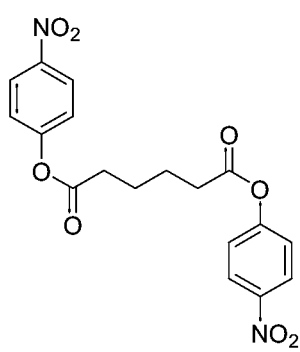

Bis-(4-nitrophenyl)adipate

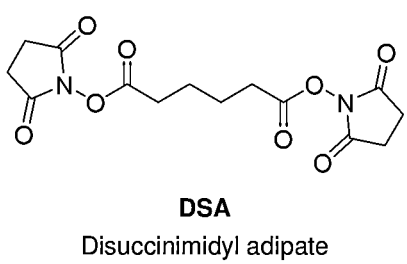

DSA
Disuccinimidyl adipate

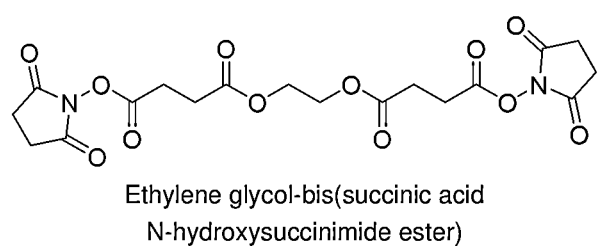

Ethylene glycol-bis(succinic acid
N-hydroxysuccinimide ester)

METHOD AND DEVICE FOR PRODUCING SACCHARIDES AND SACCHARIDE ARRAYS

FIELD OF THE INVENTION

The present invention relates to a method and a device for producing saccharides and saccharide arrays. Said method is particularly useful for the synthesis of saccharides in parallel and of high-density saccharide arrays, such as microarrays, which are required for high-throughput screenings.

BACKGROUND OF THE INVENTION

High-throughput screenings of large chemical libraries with hundreds of thousands to millions of different molecules are established as a standard method in drug discovery. The screening of highly diverse and large chemical libraries for molecular interactions promises the discovery of new drug candidates or, in the case of carbohydrate and peptide libraries, for example, the identification of new biomarkers for the development of diagnostics or vaccines. However, the costs for the synthesis of complex chemical substance libraries are very high (up to thousands of euros per substance), so that only larger pharmaceutical companies have access to such complex chemical libraries. This prevents advancements in both fundamental research (e.g., understanding development of immunity or disease progression), as well as applied research and development (e.g., new biomarkers). Therefore, there is a high demand for a cost-efficient method for synthesizing minute amounts of chemical compounds on demand and for performing miniaturized and highly parallelized screenings.

Traditionally, the synthesis of structurally defined complex saccharides has been very laborious and challenging. Compared to nucleic acids and proteins, saccharides are structurally the most diverse molecules. In 2001, Seeberger et al. reported the first automated chemical synthesis of oligosaccharides on a solid-phase synthesizer (Science 2001, 291, 1523). Since then, the process has been steadily improved, giving access to many different saccharides. However, the process is still limited for complex molecular libraries since each saccharide has to be generated sequentially and step-wise one by one, either via isolation from natural sources or chemical/chemoenzymatic synthesis. These time-consuming approaches can currently offer a selection of only a few hundred saccharides. In addition, the complexity of saccharides exceeds by far the chemical complexity of oligonucleotides (4 nucleotides) and peptides (20 amino acids). A theoretical 6-mer nucleotide has 4 096 (46) different variants, a 6-mer peptide 64 million (206), and a 6-mer saccharide may adopt over 192 billion (766) different possible configurations. This is not only due to the higher number of building blocks, but also different linkages and branching are possible. Thus, in contrast to peptide and oligonucleotide synthesis, until today, there is no high-throughput synthesis method available.

Saccharides are an important class of vaccines and antibody binders. However, the exact structures are often unknown, due to the lack of availability (*Chem Biol*, 2014, 38-50). High-density saccharide arrays are therefore required to detect these important antibodies and distinguish between those that fight infection and those that are harmful: The cost-effective access to high-density saccharide array would allow (i) the identification of valuable biomarkers for diagnostics, such as a saccharide derived from an antibiotic-resistant bacterium that binds to an antibody, (ii) would lead to improved diagnostics of the course of a disease (by identifying newly formed antibodies in a patient that correlate with disease status), (iii) would facilitate the development of rationally designed vaccines (by identifying antibodies and their glycan targets in immune patients), and, (iv) would assist finding new targets for therapy (e.g., by identifying damage-inducing autoantibodies).

So far, a cost-efficient process for parallelized high-throughput synthesis of saccharide libraries is not available.

Thus, it is the objective of the present invention to provide a cost-effective and efficient method for high-throughput synthesis of saccharides.

The objective of the present invention is solved by the teaching of the independent claims. Further advantageous features, aspects and details of the invention are evident from the dependent claims, the description, the figures, and the examples of the present application.

DESCRIPTION OF THE INVENTION

There is a long-felt need for a cost-effective and efficient method for high-throughput synthesis of saccharides. To this extent, the inventors have established a parallelized high-throughput saccharide synthesis on a solid support by first applying the saccharide building blocks on the solid support and subsequently carrying out the coupling reaction. The coupling reaction, such as a glycosylation reaction, is carried out by exposing the saccharide building blocks applied on the solid support to a vapor comprising a solvent and a coupling reagent at low temperatures. The vapor condenses on the solid support and initiates the coupling reaction, thereby allowing the simultaneous synthesis of different saccharides at discrete locations on the solid support.

Thus, the present invention is directed to a method for synthesizing saccharides comprising the steps:
 A) providing a solid support with at least one immobilized acceptor group for reacting with a saccharide;
 B) delivering the saccharide onto the solid support;
 C) applying a vapor of a mixture of a glycosylation reagent in a solvent onto the solid support at a temperature below 20° C. in order to initiate a coupling reaction of the saccharide to the at least one immobilized acceptor group.

Reworded, the present invention is directed to a method for synthesizing saccharides comprising the steps:
 A) providing a solid support with at least one immobilized acceptor group for reacting with a saccharide;
 B) delivering the saccharide onto the solid support;
 C) applying a vapor of a solution of a glycosylation reagent in a solvent onto the solid support at a temperature below 20° C. in order to initiate a coupling reaction of the saccharide to the at least one immobilized acceptor group.

Also, the present invention is directed to a method for synthesizing saccharides comprising the steps:
 A) providing a solid support with at least one immobilized acceptor group for reacting with a saccharide;
 B) delivering the saccharide onto the solid support;
 C) applying a vapor comprising a glycosylation reagent onto the solid support at a temperature below 20° C. in order to initiate a coupling reaction of the saccharide to the at least one immobilized acceptor group.

The inventors found out that under these reaction conditions the applied saccharide building blocks do not migrate or dissipate on the solid support, thereby a pattern or array of the applied saccharides is maintained, which renders the present invention particularly useful for the provision of saccharide arrays, particularly high-density saccharide arrays having a pitch of less than 300 μm.

Thus, the present invention is also directed to a method for synthesizing saccharides comprising the steps:
A) providing a solid support with at least one immobilized acceptor group for reacting with a saccharide;
B) delivering the saccharide onto the solid support;
C) applying a vapor of a solution of a glycosylation reagent in a solvent onto the solid support at a temperature below 20° C. in order to initiate a coupling reaction of the saccharide to the immobilized acceptor group.

wherein the immobilized acceptor group is located at discrete locations forming an array on the solid support.

Reworded, the present invention is directed to a method for producing saccharide arrays comprising the steps:
A) providing a solid support with at least one immobilized acceptor group for reacting with a saccharide at discrete locations;
B) delivering the saccharide onto the discrete locations of the solid support;
C) applying a vapor of a solution of a glycosylation reagent in a solvent onto the solid support at a temperature below 20° C. in order to initiate a coupling reaction of the saccharide to the immobilized acceptor group.

In a preferred embodiment the coupling reaction in step C) is carried out at a temperature below 5° C., more preferably below 0° C., more preferably between −78° C. and 0° C. and most preferably between −20° C. and 0° C., due to the high reactivity of the glycosylation reagent. Thus, the present invention is directed to a method for synthesizing saccharides comprising the steps:
A) providing a solid support with at least one immobilized acceptor group for reacting with a saccharide;
B) delivering the saccharide onto the solid support;
C) applying a vapor of a solution of a glycosylation reagent in a solvent onto the solid support at a temperature below 5° C., more preferably below 0° C., more preferably between −78° C. and 0° C. and most preferably between −20° C. and 0° C. in order to initiate a coupling reaction of the saccharide to the at least one immobilized acceptor group.

Reworded, present invention is directed to a method for synthesizing saccharides comprising the steps:
A) providing a solid support with at least one immobilized acceptor group for reacting with a saccharide;
B) delivering the saccharide onto the solid support;
C) Initiating a coupling reaction of the saccharide to the at least one immobilized acceptor group by exposing the solid support to a vapor of a solution of a glycosylation reagent in a solvent at a temperature below 20° C.

In a preferred embodiment, the ratio of the solvent and the glycosylation reagent in the vapor is in the range of 1:10 to 100,000:1. Thus, the present invention is directed to a method for synthesizing saccharides comprising the steps:
A) providing a solid support with at least one immobilized acceptor group for reacting with a saccharide;
B) delivering the saccharide onto the solid support;
C) applying a vapor of a solution of a glycosylation reagent in a solvent onto the solid support at a temperature below 20° C. in order to initiate a coupling reaction of the saccharide to the at least one immobilized acceptor group; wherein the ratio of the solvent and the glycosylation reagent in the vapor is in the range of 1:10 to 100,000:1.

In a preferred embodiment, the solvent used for the vapor is an aprotic organic solvent. Preferably, the solvent is selected from: methylene chloride, acetonitrile, chloroform, diethyl ether, 1,4-dioxane, methyl tert-butyl ether, toluene and ethyl acetate. Thus, the present invention is directed to a method for synthesizing saccharides comprising the steps:
A) providing a solid support with at least one immobilized acceptor group for reacting with a saccharide;
B) delivering the saccharide onto the solid support;
C) applying a vapor of a solution of a glycosylation reagent in a solvent onto the solid support at a temperature below 20° C. in order to initiate a coupling reaction of the saccharide to the at least one immobilized acceptor group; wherein the solvent is an aprotic organic solvent selected from: methylene chloride, acetonitrile, chloroform, diethyl ether, 1,4-dioxane, methyl tert-butyl ether, toluene and ethyl acetate.

In a preferred embodiment, the glycosylation reagent, used in the herein described methods, is a Lewis acid. Preferably, the glycosylation reagent is selected from: AgOTf, $BF_3 \cdot OEt_2$, trimethylsilyl trifluoromethanesulfonate (TMSOTf), trifluoromethanesulfonic acid (TfOH), trifluoromethanesulfonic anhydride ($Tf_2O$, triflic anhydride), lanthanoid(III) triflates, NIS/AgOTf, NIS/TfOH or dimethyl (methylthio)-sulfonium trifluoromethanesulfonate (DMTST). More preferably, the glycosylation reagent is selected from: trimethylsilyl trifluoromethanesulfonate (TMSOTf), trifluoromethanesulfonic acid (TfOH), trifluoromethanesulfonic anhydride ($Tf_2O$, triflic anhydride), and NIS/TfOH. Thus, the present invention is directed to a method for synthesizing saccharides comprising the steps:
A) providing a solid support with at least one immobilized acceptor group for reacting with a saccharide;
B) delivering the saccharide onto the solid support;
C) applying a vapor of a solution of a glycosylation reagent in a solvent onto the solid support at a temperature below 20° C. in order to initiate a coupling reaction of the saccharide to the at least one immobilized acceptor group; wherein the glycosylation reagent is a Lewis acid selected from: AgOTf, $BF_3 \cdot OEt_2$, trimethylsilyl trifluoromethanesulfonate (TMSOTf), trifluoromethanesulfonic acid (TfOH), trifluoromethanesulfonic anhydride ($Tf_2O$, triflic anhydride), lanthanoid(III) triflates, NIS/AgOTf, NIS/TfOH or dimethyl (methylthio)sulfonium trifluoromethanesulfonate (DMTST).

The term "delivering the saccharide onto the solid support" refers preferably to a solution of the saccharide which is applied onto the solid support. Thus, the term "delivering the saccharide onto the solid support" as used herein can, for the preferred embodiments, be replaced by the term "applying a solution of the saccharide onto the solid support". Thereafter the solid support is dried by evaporating the solvent. After the drying process or the solvent evaporation process, the saccharide remains on the solid support but without solvent so that free moving of the saccharide in a solvent is no longer possible.

In a preferred embodiment, the saccharide, used in the herein described methods, is a protected glycosyl donor comprising a glycal, epoxide or orthoester group or a protected glycosyl donor having a leaving group at the reducing end. Preferably, the leaving group is selected from: halogen, —O—C(=NH)—$CCl_3$, —O—C(=NPh)—$CF_3$, —OAc, —$SR^5$, —SO-Ph, —$SO_2$-Ph, —O—$(CH_2)_3$—CH=$CH_2$, —O—P$(OR^5)_2$, —O—PO$(OR^5)_2$, —O—CO—OR, —O—CO—$SR^5$, —O—CS—$SR^5$, —O—CS—$OR^5$,

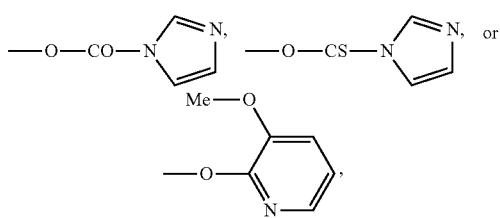

wherein $R^5$ represents an alkyl or aryl group. More preferably, the leaving group is selected from: halogen, —O—C(=NH)—CCl$_3$, —O—C(=NPh)—CF$_3$, —O—(CH$_2$)$_3$—CH=CH$_2$, —OAc, and —SR$^5$, wherein $R^5$ represents an alkyl or aryl group. Thus, the present invention is directed to a method for synthesizing saccharides comprising the steps:

A) providing a solid support with at least one immobilized acceptor group for reacting with a saccharide;

B) delivering the saccharide onto the solid support;

C) applying a vapor of a solution of a glycosylation reagent in a solvent onto the solid support at a temperature below 20° C. in order to initiate a coupling reaction of the saccharide to the at least one immobilized acceptor group; wherein the saccharide is a protected glycosyl donor having a leaving group at the reducing end selected from halogen, —O—C(=NH)—CCl$_3$, —O—C(=NPh)—CF$_3$, —OAc, —SR$^5$, —SO-Ph, —SO$_2$-Ph, —O—(CH$_2$)$_3$—CH=CH$_2$, —O—P(OR$^5$)$_2$, —O—PO(OR$^5$)$_2$, —O—CO—OR$^5$, —O—CO—SR$^5$, —O—CS—SR$^5$, —O—CS—OR$^5$,

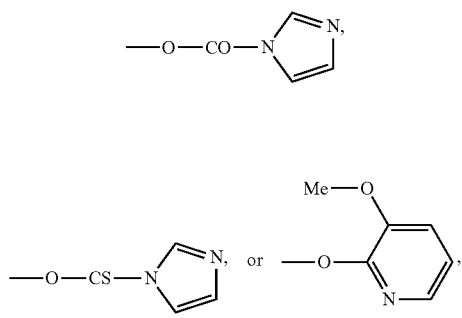

wherein $R^5$ represents an alkyl or aryl group.

In step B) of the herein described methods the saccharide can be delivered or applied or deposited or transferred with any known method from the art onto the solid support. This includes delivering the saccharide as a solid, from a solution or in a polymer matrix onto the solid support.

Thus, in one embodiment the method for synthesizing saccharides comprises the steps:

A) providing a solid support with at least one immobilized acceptor group for reacting with a saccharide;

B) delivering the saccharide onto the solid support;

C) applying a vapor of a solution of a glycosylation reagent in a solvent onto the solid support at a temperature below 20° C. in order to initiate a coupling reaction of the saccharide to the at least one immobilized acceptor group; wherein in step B) the saccharide is present as a solid, in a solution or in a polymer matrix onto the solid support.

In a further embodiment the method for synthesizing saccharides comprises the steps:

A) providing a solid support with at least one immobilized acceptor group for reacting with a saccharide;

B) applying a solution of a saccharide onto the solid support;

C) applying a vapor of a solution of a glycosylation reagent in a solvent onto the solid support at a temperature below 20° C. in order to initiate a coupling reaction of the saccharide to the at least one immobilized acceptor group.

In a preferred embodiment, the delivered saccharide is dried prior to initiating the coupling reaction in step C) in order to obtain higher reaction yields and less side products due to any water or moisture present. The saccharide is dried under reduced pressure and/or heating. Thus, the present invention is directed to a method for synthesizing saccharides comprising the steps:

A) providing a solid support with at least one immobilized acceptor group for reacting with a saccharide;

B) delivering the saccharide onto the solid support;

C') drying the solid support obtained in step B) under reduced pressure and/or heating; and C) applying a vapor of a solution of a glycosylation reagent in a solvent onto the solid support at a temperature below 20° C. in order to initiate a coupling reaction of the saccharide to the at least one immobilized acceptor group.

When the saccharide is applied in a solution onto the solid support, the solvent is evaporated in the drying step C'). Thus, in one embodiment the method for synthesizing saccharides comprises the steps:

A) providing a solid support with at least one immobilized acceptor group for reacting with a saccharide;

B) applying a solution of a saccharide onto the solid support;

C') evaporating the solvent of the solution of the saccharide under reduced pressure and/or heating; and C) applying a vapor of a solution of a glycosylation reagent in a solvent onto the solid support at a temperature below 20° C. in order to initiate a coupling reaction of the saccharide to the at least one immobilized acceptor group.

DETAILED DESCRIPTION OF THE INVENTION

Definitions

As used herein, the term "saccharide" refers to but is not restricted to monosaccharide, disaccharide, trisaccharide, tetrasaccharide, pentasaccharide, hexasaccharide, heptasaccharide, octasaccharide, oligosaccharide, polysaccharide and glycan. The saccharide comprises preferably at least one of monosaccharide units selected from:

D-Arabinose, D-Lyxose, D-Ribose, D-Xylose, L-Arabinose, L-Lyxose, L-Ribose, L-Xylose, D-Ribulose, D-Xylulose, L-Ribulose, L-Xylulose, D-Deoxyribose, L-Deoxyribose, D-Erythrose, D-Threose, L-glycero-D-manno-Heptose, D-glycero-D-manno-Heptose, D-Allose, D-Altrose, D-Glucose, D-Mannose, D-Gulose, D-Idose, D-Galactose, D-Talose, D-psicose, D-fructose, D-sorbose, D-tagatose, 6-Deoxy-L-altrose, 6-Deoxy-D-talose, D-Fucose, L-Fucose, D-Rhamnose, L-Rhamnose, D-Quinovose, Olivose, Tyvelose, Ascarylose, Abequose, Paratose, Digitoxose, Colitose, D-Glucosamine, D-Galactosamine, D-Mannosamine, D-Allosamine, L-Altrosamine, L-fucosamine, D-Gulosamine, L-Idosamine, D-Talosamine, N-Acetyl-D- glucosamine, N-Acetyl-D-galactosamine, N-Acetyl-D-mannosamine, N-Acetyl-D-allosamine, N-Acetyl-L-altrosamine, N-Acetyl-D-gulosamine, N-Acetyl-L-idosamine, N-Acetyl-D-talosamine, N-Acetyl-D-fucosamine, N-Acetyl-L-fucosamine, N-Acetyl-L-rhamnosamine, N-Acetyl-D-quinovosamine, D-Glucuronic acid, D-Galacturonic acid, D-Mannuronic acid, D-Alluronic acid, L-Altruronic acid, D-Guluronic acid, L-Guluronic acid, L-Iduronic acid, D-Taluronic acid, Neuraminic acid, N-Acetylneuraminic acid, N-Glycolylneuraminic acid, Apiose, Bacillosamine, Thevetose, Acofriose, Cymarose, Muramic acid, N-Acetylmuramic acid, N-Glycolylmuramic acid, 3-Deoxy-lyxo-heptulosaric acid, Ketodeoxyoctonic acid, 3-deoxy-D-manno-oct-2-ulosonic acid (KDO) and Ketodeoxynononic acid. Preferably the monosaccharides, and the monosaccharide units belong to the following group of α- and β-D/L-carbohydrates comprising or consisting of:

α-D-ribopyranose, α-D-arabinopyranose, α-D-xylopyranose, α-D-lyxopyranose, α-D-allopyranose, α-D-altropyranose, α-D-glucopyranose, α-D-mannpyranose, α-D-glucopyranose, α-D-idopyranose, α-D-galactopyranose, α-D-talopyranose, α-D-psicopyranose, α-D-fructopyranose, α-D-sorbopyranose, α-D-tagatopyranose, α-D-ribofuranose, α-D-arabinofuranose, α-D-xylofuranose, α-D-lyxofuranose, α-D-Allofuranose, α-D-Altrofuranose, α-D-Glucofuranose, α-D-Mannofuranose, α-D-gulofuranose, α-D-idofuranose, α-D-galactofuranose, α-D-talofuranose, α-D-psicofuranose, α-D-fructofuranose, α-D-sorbofuranose, α-D-tagatofuranose, α-D-xylulofuranose, α-D-ribulofuranose, α-D-threofuranose, α-D-rhamnopyranose, α-D-erythrofuranose, α-D-glucosamine, α-D-galactosamine, α-D-mannosamine, N-acetyl-α-D-glucosamine, N-acetyl-α-D-galactosamine, N-acetyl-α-D-mannosamine, α-D-glucopyranuronic acid, β-D-ribopyranose, β-D-arabinopyranose, β-D-xylopyranose, β-D-lyxopyranose, β-D-allopyranose, β-D-altropyranose, β-D-glucopyranose, β-D-mannpyranose, β-D-glucopyranose, β-D-idopyranose, β-D-galactopyranose, β-D-talopyranose, β-D-psicopyranose, β-D-fructopyranose, β-D-sorbopyranose, β-D-tagatopyranose, β-D-ribofuranose, β-D-arabinofuranose, β-D-xylofuranose, β-D-lyxofuranose, β-D-rhamnopyranose, β-D-allofuranose, β-D-altrofuranose, β-D-glucofuranose, β-D-mannofuranose, β-D-gulofuranose, β-D-idofuranose, β-D-galactofuranose, β-D-talofuranose, β-D-psicofuranose, β-D-fructofuranose, β-D-sorbofuranose, β-D-tagatofuranose, β-D-xylulofuranose, β-D-ribulofuranose, β-D-threofuranose, β-D-erythrofuranose, β-D-glucosamine, β-D-glucopyranuronic acid, α-L-ribopyranose, α-L-arabinopyranose, α-L-xylopyranose, α-L-lyxopyranose, α-L-allopyranose, α-L-altropyranose, α-L-glucopyranose, α-L-mannpyranose, α-L-glucopyranose, α-L-idopyranose, α-L-galactopyranose, α-L-talopyranose, α-L-psicopyranose, α-L-fructopyranose, α-L-sorbopyranose, α-L-tagatopyranose, α-L-rhamnopyranose, α-L-ribofuranose, α-L-arabinofuranose, α-L-xylofuranose, α-L-lyxofuranose, α-L-Allofuranose, α-L-Altrofuranose, α-L-Glucofuranose, α-L-Mannofuranose, α-L-gulofuranose, α-L-idofuranose, α-L-galactofuranose, α-L-talofuranose, α-L-psicofuranose, α-L-fructofuranose, α-L-sorbofuranose, α-L-tagatofuranose, α-L-xylulofuranose, α-L-ribulofuranose, α-L-threofuranose, α-L-erythrofuranose, α-L-glucosamineα-L-glucopyranuronic acid, α-L-fucosamine, α-L-rhamnosamine, N-acetyl-α-L-fucosamine, N-acetyl-α-L-rhamnosamine, β-L-ribopyranose, β-L-arabinopyranose, β-L-xylopyranose, β-L-lyxopyranose, β-L-allopyranose, β-L-altropyranose, β-L-glucopyranose, β-L-mannpyranose, β-L-glucopyranose, β-L-idopyranose, β-L-galactopyranose, β-L-talopyranose, β-L-psicopyranose, β-L-fructopyranose, β-L-sorbopyranose, β-L-tagatopyranose, β-L-ribofuranose, β-L-arabinofuranose, β-L-xylofuranose, β-L-lyxofuranose, β-L-allofuranose, β-L-altrofuranose, β-L-glucofuranose, β-L-mannofuranose, β-L-gulofuranose, β-L-idofuranose, β-L-galactofuranose, β-L-talofuranose, β-L-psicofuranose, β-L-fructofuranose, β-L-sorbofuranose, β-L-tagatofuranose, β-L-xylulofuranose, β-L-ribulofuranose, β-L-threofuranose, β-L-erythrofuranose, β-L-glucosamine, β-L-fucosamine, β-L-rhamnosamine, N-acetyl-β-L-fucosamine, N-acetyl-α-L-rhamnosamine, β-L-glucopyranuronic acid, and β-L-rhamnopyranose.

The above-mentioned saccharides, and monosaccharides, monosaccharide units are optionally protected with the appropriate protecting groups as defined below.

The saccharides are further optionally modified to carry amide, carbonate, carbamate, carbonyl, thiocarbonyl, carboxy, thiocarboxy, ester, thioester, ether, epoxy, hydroxyalkyl, alkylenyl, phenylene, alkenyl, imino, imide, isourea, thiocarbamate, thiourea and/or urea moieties.

The term "protecting group" or "protective group" as used herein refers to commonly used groups in organic synthesis, preferably used for protection of amines, hydroxyl groups, thiols, imines, carbonyls, carboxyls or other common functional groups, and particularly preferred for amines and hydroxyl groups. The protecting groups are characterized in that they are stable under reaction conditions applied during the synthesis, i.e. they are not cleaved off or undergo undesired side reactions and prevent any reaction of the protected functional group they are bonded to. Additionally, the protecting groups are selected to not hinder or to not affect the performed reaction steps in terms of yield or stereoselectivity.

Preferred protecting groups for hydroxyl groups are acetyl, phenyl, benzyl, isopropylidene, benzylidene, benzoyl, p-methoxybenzyl, p-methoxybenzylidene, p-methoxyphenyl, p-bromobenzylidene, p-nitrophenyl, allyl, allyloxycarbonyl, monochloroacetyl, isopropyl, p-bromobenzyl, dimethoxytrityl, trityl, 2-naphthylmethyl, pivaloyl, triisopropylsilyl, tert-butyldimethylsilyl, tert-butyldiphenylsilyl, tert-butylmethoxyphenylsilyl, triethylsilyl, trimethylsilyl, 2-trimethylsilylethoxymethyl, 9-fluorenylmethoxycarbonyl, tert-butyloxycarbonyl, benzyloxymethyl, m ethyloxymethyl, tert-butyloxymethyl, methoxyethyloxymethyl, and levulinoyl.

Preferred protecting groups for amine groups are acetyl, benzyl, p-methoxyphenyl, benzoyl, p-methoxybenzyl, 3,4-dimethoxybenzyl, benzyloxycarbonyl(Cbz), allyloxycarbonyl, trichloroacetyl (TCA), trifluoroacetyl, trichloroethyl (Troc), p-bromobenzyl, dimethoxytrityl, trityl, 2-naphthylmethyl, pivaloyl, 9-fluorenylmethoxycarbonyl (Fmoc), tert-butyloxycarbonyl(BOC), levulinoyl, tosyl, nosyl, 2-nitrophenylsulfenyl (Nps), and phthalimidyl.

The protecting groups can be differentiated in "permanent protecting groups" and "temporary protecting groups". Permanent protecting groups are protecting groups that are stable during the entire synthesis and that can be efficiently removed at the late stage of the synthesis. In this case, permanent protecting groups are masking the hydroxyl groups and amino groups, if present, during the entire synthesis. Preferably permanent protecting groups are benzyl, benzoyl, acetyl, allyloxycarbonyl (alloc) and benzyloxycarbonyl group (Cbz).

The temporary protecting groups are generally orthogonal protecting groups that can be selectively removed at different levels of the synthesis to free hydroxyl groups for subsequent introduction of different substituents, including monosaccharides, other protecting groups or other residues present on the molecule. Temporary protecting groups are preferably selected from, but are not restricted to: allyl, p-methoxybenzyl, 2-naphthylmethyl, tri-isopropylsilyl, tert-butyldimethylsilyl, tert-butylmethoxyphenylsilyl, triethylsilyl, trimethylsilyl, 2-trimethylsilylethoxymethyl, 9-fluorenylmethoxycarbonyl and levulinoyl.

The ingenious choice of protecting groups allows expedient access to a library of saccharides. It is apparent for a skilled person to choose the protecting groups in such a manner that they can be removed from the saccharide without cleaving the saccharide from the solid support.

As used herein the term "donor" or "glycosyl donor" refers to a saccharide that forms a glycal, or a saccharide comprising an epoxide or orthoester group or a saccharide that contains a leaving group at the reducing end. Suitable leaving groups include halogen, —O—C(=NH)—CCl$_3$, —O—C(=NPh)—CF$_3$, —OAc, —SR$^5$, —SO-Ph, —SO$_2$-Ph, —O—(CH$_2$)$_3$—CH=CH$_2$, —O—P(OR$^5$)$_2$, —O—PO(OR$^5$)$_2$, —O—CO—OR$^5$, —O—CO—SR$^5$, —O—CS—SR$^5$, —O—CS—OR$^5$,

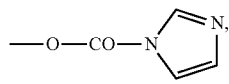

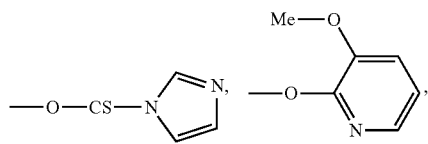

wherein R$^5$ may be any alkyl or aryl group.

As used herein the term "acceptor" or "glycosyl acceptor" refers to a saccharide that contains at least one free hydroxy or amine function and is capable of forming a glycosidic bond with a glycosyl donor under suitable reaction conditions.

As used herein the term "saccharide building block" or "building block" refers to a saccharide acceptor or saccharide donor, i.e. to a saccharide that is capable of forming a glycosidic bond when being exposed to a vapor comprising a solution of a glycosylating agent. The saccharide building block can be fully protected (i.e. each hydroxy or amino group is blocked by a protecting group), partially protected (i.e. at least one hydroxy or amino groups is blocked by a protecting group) or unprotected (i.e. none of hydroxy or amino groups is blocked by a protecting group). For forming an amide bond with an anchoring group present on the solid support the saccharide building block may also be modified at the reducing end with a suitable functional group such as a carboxylic acid (e.g. hydroxyacetate), azide, alkyne, thiol or an amine (e.g. aminopropyl or aminopentyl). Any known saccharide building block can be employed in the inventive methods described herein, including saccharides, glycopeptides or glycopeptoids as described in Beilstein J. Org. Chem. 2014, 10, 2453-2460.

The term "coupling reaction", as used herein, refers to reactions between a glycosyl donor and a glycosyl acceptor, wherein the reducing end of the donor reacts with a free hydroxy or amine group of the acceptor. Thus, O-glycosylation or N-glycosylation methods are preferably employed in the coupling reaction of the method according to the invention. More preferably, O-glycosylation methods are employed in the coupling reaction of the method according to the invention. These glycosylation methods are known from the state of the art. Generally, they require a leaving group at the reducing end of the donor, which is activated in the presence of a catalyst. The glycosylation reactions take place upon treatment of a donor and an acceptor with a "glycosylation reagent" which acts as an activator or an activating agent. Glycosylation reagents known to the skilled person include, but are not restricted to: AgOTf, BF$_3$·OEt$_2$, trimethylsilyl trifluoromethanesulfonate (TMSOTf), trifluoromethanesulfonic acid (TfOH), trifluoromethanesulfonic anhydride (Tf$_2$O, triflic anhydride), lanthanoid(III) triflates, NIS/AgOTf, NIS/TfOH or dimethyl (methylthio)-sulfonium trifluoromethanesulfonate (DMTST).

The term "solid support" as used herein refers to an insoluble, functionalized, polymeric material to which saccharides or other reagents may be attached or immobilized, directly or via a linker bearing an anchoring group, allowing saccharides to be readily separated (by washing, filtration, centrifugation, etc.) from excess reagents, soluble reaction by-products, or solvents. The solid support has preferably the form of a plate or a membrane.

As used herein, the term "saccharide array" is understood as meaning a saccharide library bound to a solid support, wherein the saccharide library includes the totality of many different saccharides bound to defined sites of the solid support, the so called discrete locations or spots. The term "glycan array" is uses synonymously to saccharide array.

As used herein, the term "high-density saccharide array" refers to a saccharide array having a pitch of preferably less than 300 μm, more preferably less than 200 μm, more preferably less than 150 μm and most preferably less than 100 μm. The pitch is defined by the spacing of individual locations or spots measured from the midpoint.

"Alkyl" refers to saturated hydrocarbon groups of from 1 to 18 carbon atoms, either straight chained or branched, more preferably from 1 to 8 carbon atoms, and most preferably 1 to 6 carbon atoms. An alkyl with a specified number of carbon atoms is denoted as C$_1$-C$_8$ alkyl and refers to a linear C$_1$-C$_8$ alkyl of —CH$_3$, —C$_2$H$_5$, —C$_3$H$_7$, —C$_4$H$_9$, —C$_8$H$_{17}$, —CH$_2$-Ph, —CH$_2$—CH$_2$-Ph or a branched C$_1$-C$_8$ alkyl or preferably branched C$_3$-C$_8$ alkyl of —CH(CH$_3$)$_2$, —CH$_2$—CH(CH$_3$)$_2$, —CH(CH$_3$)—C$_2$H$_5$, —C(CH$_3$)$_3$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —C$_4$H$_8$—CH(CH$_3$)$_2$, —C$_3$H$_6$—CH(CH$_3$)—C$_2$H$_5$, —C$_3$H$_6$—CH(CH$_3$)—C$_2$H$_5$, —C$_2$H$_4$—CH(CH$_3$)—C$_3$H$_7$, —CH$_2$—CH(CH$_3$)—C$_4$H$_9$, —CH(CH$_3$)—C$_6$H$_{11}$, —CH(C$_2$H$_5$)—C$_4$H$_9$, —C$_2$H$_4$—CH(CH$_3$)—C$_3$H$_7$, —CH$_2$—CH(C$_2$H$_5$)—C$_3$H$_7$, —CH$_2$—CH(CH$_3$)—C$_4$H$_9$, —CH$_2$—CH (CH₃)—CH₂—CH(CH₃)₂, —CH(C₂H₅)—CH₂—CH(CH₃)₂, —CH(CH₃)—C₂H₄—CH(CH₃)₂, —CH(CH₃)—CH₂—CH(CH₃)—C₂H₅, —CH₂—CH(CH₃)—CH(CH₃)—C₂H₅, —CH(CH₃)—CH₂—CH(CH₃)—C₂H₅, —CH(CH₃)—CH(C₂H₅)—C₂H₅, —CH(C₂H₅)—CH(CH₃)—C₂H₅, —CH(CH₃)—CH(CH₃)—C₃H₇, —C₂H₄—CH(CH₃)—CH(CH₃)₂, —CH₂—CH(C₂H₅)—CH(CH₃)₂, —CH₂—CH(CH₃)—CH₂—CH(CH₃)₂, —CH₂—CH(CH₃)—CH(CH₃)—C₂H₅, —C₂H₄—C(CH₃)₂—C₂H₅, —CH₂—C(CH₃)(C₂H₅)₂, —CH₂—C(CH₃)₂—C₃H₇, —CH₂—C(CH₃)₂—C₃H₇, —C(CH₃)(C₂H₅)—C₃H₇, —C(CH₃)₂—C₄H₉, —CH₂—C(CH₃)₂—CH(CH₃)₂, —C(CH₃)(C₂H₅)—CH(CH₃)₂, —C(CH₃)₂—CH₂—CH(CH₃)₂, —C(CH₃)₂—C(CH₃)₃, —C(CH₃)₂—CH(CH₃)—C₂H₅, —C₃H₆—C(CH₃)₃, —C₂H₄—C(CH₃)₂—C₂H₅, —CH₂—CH(CH₃)—C(CH₃)₃, —CH(C₂H₅)—C(CH₃)₃, —CH(CH₃)—CH₂—C(CH₃)₃, —CH(CH₃)—C(CH₃)₂—C₂H₅, —O₅H₁₀—CH(CH₃)₂, —C₄H₈—C(CH₃)₃, —C₄H₈—CH(CH₃)—C₂H₅, —C₄H₈—CH(CH₃)—C₂H₅, —C₃H₆—C(CH₃)₂—C₂H₅, —C₃H₆—CH(C₂H₅)—C₂H₅, —C₃H₆—CH(CH₃)—C₃H₇, —C₂H₄—C(CH₃)₂—C₃H₇, —C₂H₄—CH(C₂H₅)—C₃H₇, —C₂H₄—CH(CH₃)—C₄H₉, —CH₂—C(CH₃)₂—C₄H₉, —CH₂—CH(C₂H₅)—C₄H₉, —CH₂—CH(CH₃)—C₆H₁₁, —C(CH₃)₂—C₆H₁₁, —CH(CH₃)—C₆H₁₃, —CH(C₃H₇)—C₄H₉, —CH(C₂H₅)-05H₁₁, —CH₂—C(CH₃)(C₂H₅)—C₃H₇, —C₂H₄—CH(CH₃)—CH₂—CH(CH₃)₂, —CH₂—C(CH₃)₂—CH₂—CH(CH₃)₂, —CH₂—CH(C₂H₅)—CH₂—CH(CH₃)₂, —CH₂—CH(CH₃)—C₂H₄—CH(CH₃)₂, —CH₂—CH(CH₃)—CH₂—C(CH₃)₃, —CH₂—CH(CH₃)—CH₂—CH(CH₃)—C₂H₅, —C(CH₃)(C₂H₅)—CH₂—CH(CH₃)₂, —CH(C₃H₇)—CH₂—CH(CH₃)₂, —CH(C₂H₅)—C₂H₄—CH(CH₃)₂, —CH(C₂H₅)—CH₂—C(CH₃)₃, —CH(C₂H₅)—CH₂—CH(CH₃)—C₂H₅, —CH₂—CH(CH₃)—C₂H₄—CH(CH₃)₂, —C(CH₃)₂—C₂H₄—CH(CH₃)₂, —CH(C₂H₅)—C₂H₄—CH(CH₃)₂, —CH(CH₃)—C₃H₆—CH(CH₃)₂, —CH(CH₃)—C₂H₄—C(CH₃)₃, —CH(CH₃)—C₂H₄—CH(CH₃)—C₂H₅, —CH₂—CH(CH₃)—CH₂—CH(CH₃)—C₂H₅, —C(CH₃)₂—CH₂—CH(CH₃)—C₂H₅, —CH(CH₃)—C₂H₄—CH(CH₃)—C₂H₅, —CH(CH₃)—CH₂—C(CH₃)₂—C₂H₅, —CH(CH₃)—CH₂—CH(CH₃)—C₃H₇, —C₂H₄—CH(CH₃)—CH(CH₃)—C₂H₅, —CH₂—C(CH₃)₂—CH(CH₃)—C₂H₅, —CH₂—CH(C₂H₅)—CH(CH₃)—C₂H₅, —CH₂—CH(CH₃)—CH(CH₃)—CH(CH₃)—C₂H₅, —CH(CH₃)—CH₂—C(CH₃)₂—C₂H₅, —CH₂—CH(CH₃)—CH(CH₃)₂, —CH(CH₃)—CH(C₂H₅)—C₂H₅—, —C₃H₆—CH(CH₃)—CH(CH₃)₂, —C₂H₄—C(CH₃)₂—CH(CH₃)₂, —C₂H₄—CH(C₂H₅)—CH(CH₃)₂, —C₂H₄—CH(CH₃)—C(CH₃)₃, —C₂H₄—CH(CH₃)—CH(CH₃)—C₂H₅, —CH(CH₃)—CH(CH₃)—C₂H₅, —C₃H₆—C(CH₃)₂—C₂H₅, —C₂H₄—C(CH₃)₂—C₃H₇, —CH₂—C(CH₃)(C₂H₅)₂, —C₂H₄—C(C₂H₅)₃, —C₂H₄—C(CH₃)₂—C₃H₇, —CH₂—C(CH₃)₂—C₄H₉, —C(C₂H₅)₂—C₃H₇, —C(CH₃)(C₃H₇)—C₃H₇, —C(CH₃)(C₂H₅)—C₄H₉, —C(CH₃)(—C₂H₅)—C₄H₉, —C(CH₃)₂—C₆H₁₁, —C₂H₄—C(CH₃)₂—CH(CH₃)₂, —CH₂—C(CH₃)₂—C(CH₃)₃, —C(C₂H₅)₂—CH(CH₃)₂, —C(CH₃)(C₃H₇)—CH(CH₃)₂, —C(CH₃)(C₂H₅)—C(CH₃)₃, —CH₂—C(CH₃)₂—CH₂—CH(CH₃)₂, —C(CH₃)₂—C₂H₄—CH(CH₃)₂, —C(CH₃)₂—CH₂—C(CH₃)₃, —CH₂—C(CH₃)₂—C(CH₃)₃, —C₄H₈—C(CH₃)₃, —C₃H₆—C(CH₃)₂—C₂H₅, —C₂H₄—C(CH₃)₂—C₃H₇, —C₂H₄—CH(CH₃)—C(CH₃)₃, —CH₂—C(CH₃)₂—C(CH₃)₃.

"Aryl" refers to an unsaturated aromatic carbocyclic group of from 6 to 12 carbon atoms inclusively having a single ring (e.g., phenyl) or multiple condensed rings (e.g., naphthyl or anthryl). Exemplary aryls include phenyl, pyridyl, naphthyl and the like.

"Vapor" refers to substance or substance mixture in the gas phase at a temperature lower than its critical temperature, thereby allowing the gas to condense at increased pressure or on a surface having a lower temperature than the vapor. The vapor used in the present invention comprises at least one aprotic organic solvent and at least one glycosylation reagent. The at least one aprotic organic solvent and/or the at least one glycosylation reagent may also be present in the vapor as tiny particles of liquid, solid, or both, thus forming a suspension or aerosol or fog. The vapor is formed from a mixture or solution of at least one aprotic organic solvent at least one glycosylation reagent by heating and/or under reduced pressure. Due to the evaporation of the volatile organic solvent, the at least one glycosylation reagent moves into gas phase, too.

Solid supports for immobilization of carbohydrates or peptides are well-known in the art. Various methods for immobilization of mono- and oligosaccharides to solid supports (e.g. membrane, plates, glass plates, microarrays, etc.) are well known in the art and described in e.g. QSAR Comb. Sci. 25, 2006, No. 11, 1033-1038. Thus, any common solid support with acceptor groups or anchor groups suitable for glycan microarrays can be used within the present invention, including commercially available amino-PEG cellulose membranes, hydroxyl-modified polypropylene membranes, microarray slides, including but not restricting to Corning® epoxide coated slides or Corning® GAPS™ II coated slides, CodeLink® NHS slides, N-hydroxysuccinimide-activated, epoxy-, amino-, carboxy-, aldehyde-, thiol-, or maleimide-functionalized glass slides, CPG, or aluminium oxide. Suitable for glycan microarrays means here that the solid support, e.g. the slide or membrane, needs to be resistant under glycosylation conditions as well as during the deprotection of the orthogonal protecting groups. Finally, it also has to give the possibility to cleave the final saccharides from the membrane for subsequent applications.

Said solid supports present on their surface an acceptor group for reacting with a saccharide, i.e. a functionality that is prone to react with a hydroxy group or leaving group of a saccharide employed in the methods described herein, or with a functional group Y of an interconnecting molecule (see FIG. 4) to provide modified solid supports, presenting on their surface an acceptor group of the interconnecting molecule that can further react with a hydroxy group or leaving group of a saccharide. The acceptor groups are suitable for immobilizing saccharides on solid supports and are herein synonymously termed as "anchor groups". Suitable acceptor groups on solid supports include but are not restricted to are amino, thiol, hydroxy, N-hydroxysuccinimidyl, carboxy, oxime, epoxy or hydrazide groups (see FIG. 3).

The acceptor group may also be a saccharide, particularly a monosaccharide as listed above, or a disaccharide consisting of monosaccharide units as listed above, bound either directly or via an interconnecting molecule to the surface of the solid support. The acceptor group may also be a glycosyl acceptor comprising such a saccharide. In this case, the glycosyl acceptor forms a part of the saccharide to be synthesized. The glycosyl acceptor contains at least one free hydroxy or amine function and is capable of forming a glycosidic bond with a saccharide under suitable reaction conditions. Suitable acceptor groups are for instance 1-oxyacetates as shown in FIG. 5. Thus, it is apparent for a skilled person to choose the glycosyl acceptor depending on the saccharide to be synthesized and in such a manner that the saccharide, after synthesis, can be cleaved from the solid support.

The acceptor group may comprise a glycosyl acceptor of the following formula:

S—O-L-E wherein S represents a monosaccharide selected from

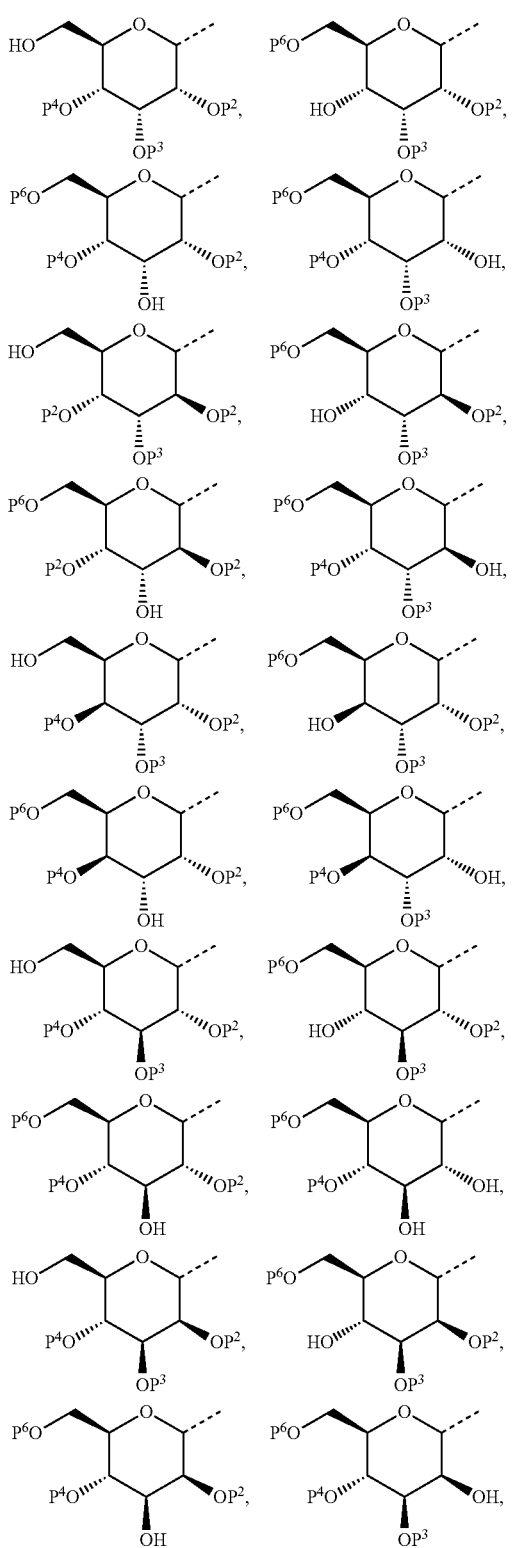
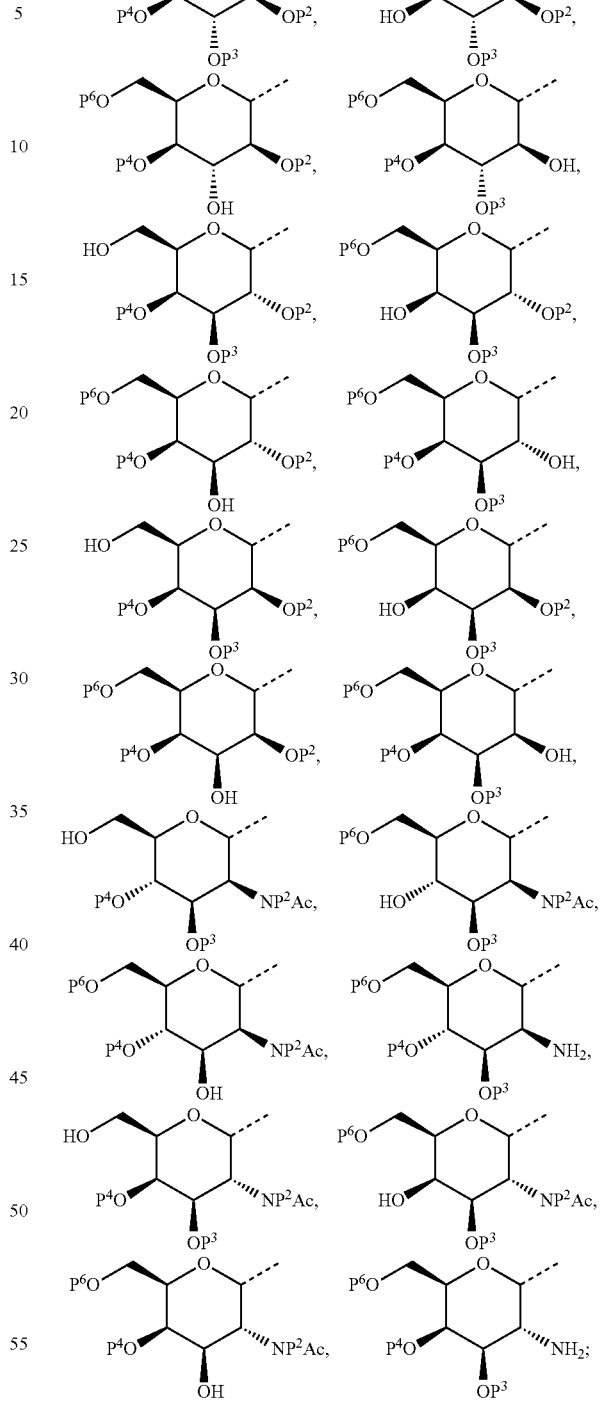

$P^2$, $P^3$, $P^4$ and $P^6$ represent independently of each other protecting groups;

L is a linker;

and E represents amino, thiol, hydroxy, N-hydroxysuccinimidyl, carboxylate, carboxylic acid, oxime, epoxy or hydrazide.

$P^2$ is a protecting group for a hydroxy group or a protecting group for an amine group, P³, P⁴ and P⁵ represent protecting groups for a hydroxyl group, wherein the protecting group for a hydroxy group is selected from the group consisting of: acetyl, phenyl, benzyl, isopropylidene, benzylidene, benzoyl, p-methoxybenzyl, p-methoxybenzylidene, p-methoxyphenyl, p-bromobenzylidene, p-nitrophenyl, allyl, allyloxycarbonyl, monochloroacetyl, isopropyl, p-bromobenzyl, dimethoxytrityl, trityl, 2-naphthylmethyl, pivaloyl, triisopropylsilyl, tert-butyldimethylsilyl, tert-butyldiphenylsilyl, tert-butylmethoxyphenylsilyl, triethylsilyl, trimethylsilyl, 2-trimethylsilylethoxymethyl, 9-fluorenylmethoxycarbonyl, tert-butyloxycarbonyl, benzyloxymethyl, methyloxymethyl, tert-butyloxymethyl, methoxyethyloxymethyl, and levulinoyl; and the protecting group for an amine group is selected from acetyl, benzyl, p-methoxyphenyl, benzoyl, p-methoxybenzyl, 3,4-dimethoxybenzyl, benzyloxycarbonyl (Cbz), al lyloxycarbonyl, trichloroacetyl (TCA), trifluoroacetyl, trichloroethyl(Troc), p-bromobenzyl, dimethoxytrityl, trityl, 2-naphthylmethyl, pivaloyl, 9-fluorenylmethoxycarbonyl (Fmoc), tert-butyloxycarbonyl(BOC), levulinoyl, tosyl, nosyl, 2-nitrophenylsulfenyl (Nps), and phthalimidyl.

Preferably, the linker -L- is selected from: $-L^a-$, $-L^a-L^e-$, $-L^a-L^b-L^e-$, $-L^a-L^d-L^e-$;
wherein
$-L^a-$ is selected from: $-(CH_2)_o-$, $-(CH_2-CH_2-O)$, $-C_2H_4-$, $-(CH_2-CH_2-O)_o-CH_2$;
$-L^b-$ represents $-O-$;
$-L^d-$ is selected from $-(CH_2)_q-$, $-(CF_2)_q-$, $-(CH_2-CH_2-O)_q-C_2H_4-$, and $-(CH_2-CH_2-O)_q-CH_2-$,
$-L^e-$ is selected from: $-(CH_2)_{p1}-$, $-(CF_2)_{p1}-$, $-C_2H_4-(O-CH_2-CH_2)_{p1}-$, $-CH_2-(O-CH_2-CH_2)_{p1}-$ and $-(CH_2)_{p1}-O-(CH_2)_{p2}-$;
and o, q, p1 and p2 are independently of each other an integer selected from 1, 2, 3, 4, 5, and 6.

More preferably, -L- represents $-(CH_2)_o-$ and o is an integer selected from 1 2, 3, 4, 5 and 6.

More preferably, -L- represents $-(CH_2)_o-$ and o is an integer selected from 1, 2, 3 and 4.

Preferably, the present invention is directed to a method for synthesizing saccharides comprising the steps:
A) providing a solid support with at least one immobilized acceptor group for reacting with a saccharide;
B) delivering the saccharide onto the solid support;
C) applying a vapor of a solution of a glycosylation reagent in a solvent onto the solid support at a temperature below 20° C. in order to initiate a coupling reaction of the saccharide to the at least one immobilized acceptor group;
wherein the solid support is an insoluble, functionalized, polymeric material to which saccharides or other reagents are attached or immobilized, directly or via a linker bearing an anchoring group, in particular, selected from amino-PEG cellulose membranes, hydroxyl-modified polypropylene membranes, and microarray slides.

Preferably, the present invention is directed to a method for synthesizing saccharides comprising the steps:
A) providing a solid support with at least one immobilized acceptor group for reacting with a saccharide;
B) delivering the saccharide onto the solid support;
C) applying a vapor of a solution of a glycosylation reagent in a solvent onto the solid support at a temperature below 20° C. in order to initiate a coupling reaction of the saccharide to the at least one immobilized acceptor group;
wherein the at least one immobilized acceptor group is amino, thiol, hydroxy, N-hydroxysuccinimidyl, carboxy, oxime, epoxy or hydrazide groups; or the at least one immobilized acceptor group has the following formula

S—O-L-E wherein S, O, L, and E have the same meanings as defined above.

The interconnecting molecule may be chosen in such a manner that it facilitates the identification of synthesized saccharides after cleavage from the solid support via mass spectrometry (MALDI-TOF-MS) by enhancing the molecular weight of the saccharide. The interconnecting molecule may also be photocleavable, such as the nitrobenzyl linker shown below, for obtaining saccharides with a free reducing end after cleavage from the solid support.

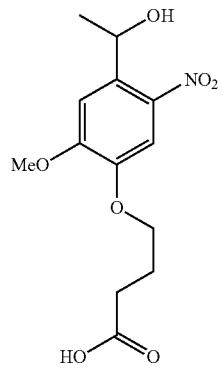 [SMILES: COc1cc(C(C)O)c([N+](=O)[O-])cc1OCCCC(=O)O]

According to the present invention, the coupling reaction is carried out by exposing the saccharide building blocks applied on the solid support to a vapor comprising a solvent and a coupling reagent at low temperatures. The vapor condenses on the solid support and initiates the coupling reaction. After washing and drying the solid support the next saccharide building block is applied on the solid support and exposed to the vapor comprising a solvent and a glycosylating agent. These steps are repeated until the desired saccharides are formed, thereby allowing the simultaneous synthesis of different saccharides at discrete locations on the solid support.

Thus, one aspect of the present invention is directed to a method for synthesizing saccharides comprising the steps:
A1) providing a solid support with acceptor groups for reacting with a saccharide,
B1) delivering a first saccharide onto the solid support;
C1) drying the solid support,
D1) applying a vapor of a solution of a glycosylation reagent in a solvent onto the solid support at a temperature below 20° C. in order to initiate a coupling reaction of the first saccharide to the acceptor group of the solid support in order to obtain a saccharide immobilized to the solid support,
E1) washing and drying the solid support,
F1) delivering a further saccharide onto the solid support;
G1) drying the solid support,
H1) applying a vapor of a solution of a glycosylation reagent in a solvent onto the solid support at a temperature below 20° C. in order to initiate the coupling reaction of the further saccharide to the saccharide immobilized to the solid support, I1) washing and drying the solid support, J1) repeating the steps F1) to I1) until the saccharide of desired length is obtained.

The method of the present invention gives access to saccharides of various lengths, including but not restricting to disaccharide, trisaccharide, tetrasaccharide, pentasaccharide, hexasaccharide, heptasaccharide, octasaccharide . . . , oligosaccharide, glycans, and polysaccharide.

The method of the present invention gives access to bacterial capsular saccharides, saccharides of a viral glycoprotein, saccharide antigens of sporozoa or parasites, saccharide antigens of pathogenic fungi, and saccharide antigens which are specific to cancer cells.

The bacterial capsular saccharides belong preferably to bacteria selected from: *Allochromatium vinosum, Acinetobacter baumanii, Bacillus anthracis, Campylobacter jejuni, Clostridium* spp., *Clostridium difficile, Citrobacter* spp., *Escherichia coli, Enterobacter* spp., *Enterococcus faecalis., Enterococcus faecium, Francisella tularensis, Haemophilus influenzae, Helicobacter pylori, Klebsiella* spp., *Klebsiella pneumoniae, Listeria monocytogenes, Moraxella catharralis, Mycobacterium tuberculosis, Neisseria meningitidis, Neisseria gonorrhoeae, Proteus mirabilis, Proteus vulgaris, Pseudomonas aeruginosa, Salmonella* spp., *Salmonella typhi, Serratia* spp., *Shigella* spp., *Stenotrophomonas maltophilia, Staphyloccocus aureus, Staphyloccocus epidermidis, Streptococcus pneumoniae, Streptococcus pyogenes, Streptococcus agalactiae, Yersina pestis*, and *Yersina enterocolitica*.

The saccharides of viral glycoproteins belong preferably to viruses selected from: Adenoviruses, Ebolavirus, Epstein-Barr-virus, Flavivirus, TBE-virus, Influenza virus, Hantavirus, human immunodeficiency virus ("HIV"), herpes simplex virus ("HSV", type 1 or 2), human herpes virus 6 (HHV-6), human Papilloma virus ("HPV", type 16 or 18), human Cytomegalovirus ("HCMV"), human hepatitis B or C virus ("HBV", Type B; "HCV", type C), Lassavirus, Lyssavirus (EBL 1 or EBL 2), Marburgvirus, Norovirus, Parvovirus B19, Pestvirus, Poliovirus, Rhinovirus, Rotaviruses, SARS-associated Coronavirus, and Varicella-Zoster virus.

The saccharide antigens of sporozoa or parasites belong preferably to sporozoa or parasites selected from:

*Babesia, Balantidium, Besnoitia, Blastocystis, Coccidia, Cryptosporidium, Cytauxzoon, Cyclospora, Dientamoeba, Eimeria, Entamoeba, Enterocytozoon*, Enzephalitozoon, *Eperythrozoon, Giardia,* Hammondia, *Isospora, Leishmania, Microsporidia, Naegleria, Plasmodium, Plasmodium falciparum, Plasmodium vivax, Plasmodium ovale, Plasmodium malariae, Plasmodium knowlesi, Pneumocystis, Schistosoma, Sarcocystis, Theileria, Trichinella, Toxoplasma, Trichomonas, Trypanosoma,* Unicaria, Cestoda, *Dipylidium, Dranunculus, Echinococcus, Fasciola, Fasciolopsis, Taenia, Ancylostoma, Ascaris, Brugia, Enterobius, Loa loa, Mansonella, Necator, Oncocerca, Strongyloides, Strongylus, Toxocara, Toxascaris, Trichuris* and Wucheria.

The saccharide antigens of fungi belong preferably to fungi selected from: *Trichophyton mentagrophytes, Trichophyton rubrum, Trichophyton interdigitale, T. schönleinii, T. verrucosum, T. violaceum, T. tonsurans, Trichophyton* spp., *M. canis, Candida albicans, C. guillermondii, C. krusei, C. parapsilosis, C. tropicalis, C. glabrata, Candida* spp., *Microsporum* spp., *Microsporum canis, Microsporum audonii, Microsporum gypseum, M. ferrugineum, Trichosporum beigelii, Trichosporum inkiin, Aspergillus niger, Alternaria, Acremonium, Fusarium*, and *Scopulariopsis*.

The saccharide antigens which are specific to cancer cells belong preferably to the group of cancers selected from:

Bladder Cancer, Breast Cancer, Colon and Rectal Cancer, Endometrial Cancer, Kidney (Renal Cell) Cancer, Leukemia, Lung Cancer Melanoma, Non-Hodgkin Lymphoma, Pancreatic Cancer, Prostate Cancer, and Thyroid Cancer.

In steps B), B1), B2), B3), F1), and F2) of the inventive methods described herein, the saccharide, first saccharide or further saccharide can be delivered onto the solid support by any conventional technique known in the art, including dipping, spraying, spotting (SPOT, Tetrahedron 48, 9217-9232 (1992)), photolithographic techniques (Nat. Commun. 5, 4785 (2014)), laser induced forward transfer (LIFT or cLIFT, Nature Communications 7:11844 (2016)), or laser printing of particles (Angew. Chem. Int. Ed. 47, 7132-7135 (2008)). It is apparent for a person skilled in the art to choose a technique for delivering saccharides that is compatible with the saccharides already delivered to the solid support, i.e. without degrading or decomposing the saccharide.

Further, in steps B), B1), B2), B3), F1) and F2) of the inventive methods described herein, the saccharide, first saccharide or further saccharide can be delivered or applied onto the solid support as a solid, in form of a solution or suspension, or in a polymer matrix. In case a solution of the saccharide is delivered, a subsequent drying step C'), C1'), C2'), or C3') should be performed in order to remove (i.e. evaporate) solvent, water or any moisture. Thus, in case the saccharide, first saccharide or further saccharide is applied in a solution onto the solid support, the drying step comprises C')/C'1)/C2')/C3') drying the solid support obtained in step B)/B1)/B2)/B3)/F1)/F2) and evaporating the solvent under reduced pressure and/or heating.

Alternatively, the drying step comprises:

C')/C'1)/C2')/C3') drying the solid support obtained in step B)/B1)/B2)/B3)/F1)/F2) and evaporating the solvent under reduced pressure and heating.

Alternatively, the drying step comprises:

C')/C'1)/C2')/C3') drying the solid support obtained in step B)/B1)/B2)/B3)/F1)/F2) and evaporating the solvent under reduced pressure.

Alternatively, the drying step comprises:

C')/C'1)/C2')/C3') drying the solid support obtained in step B)/B1)/B2)/B3)/F1)/F2) and evaporating the solvent under heating.

A drying step can nevertheless also be performed when the saccharide is delivered in any other form, such as a solid or embedded in a polymer matrix.

C')/C'1)/C2')/C3') drying the solid support obtained in step B)/B1)/B2)/B3)/F1)/F2) under reduced pressure and/or heating.

Alternatively, the drying step comprises:

C')/C'1)/C2')/C3') drying the solid support obtained in step B)/B1)/B2)/B3)/F1)/F2) under reduced pressure and heating.

Alternatively, the drying step comprises:

C')/C'1)/C2')/C3') drying the solid support obtained in step B)/B1)/B2)/B3)/F1)/F2) under reduced pressure.

Alternatively, the drying step comprises:

C')/C'1)/C2')/C3') drying the solid support obtained in step B)/B1)/B2)/B3)/F1)/F2) under heating.

Thus, in one embodiment the method for synthesizing saccharides comprises the steps:

A1) providing a solid support with acceptor groups for reacting with a saccharide, B1) applying a solution of a first saccharide onto the solid support;
C1) drying the solid support and evaporating the solvent under reduced pressure and/or heat,
D1) applying a vapor of a solution of a glycosylation reagent in a solvent onto the solid support at a temperature below 20° C. in order to initiate a coupling reaction of the first saccharide to the acceptor group of the solid support in order to obtain a saccharide immobilized to the solid support,
E1) washing and drying the solid support,
F1) applying a solution of a further saccharide onto the solid support;
G1) drying the solid support and evaporating the solvent under reduced pressure and/or heat,
H1) applying a vapor of a solution of a glycosylation reagent in a solvent onto the solid support at a temperature below 20° C. in order to initiate a coupling reaction of the further saccharide to the saccharide immobilized to the solid support,
I1) washing and drying the solid support,
J1) repeating the steps F1) to I1) until the saccharide of desired length is obtained.

Also, in steps B), B1), B2), B3), F1), and F2) of the inventive methods described herein, the saccharide, first saccharide and/or further saccharide is a saccharide building block. Preferably, the saccharide, first saccharide and/or further saccharide is a glycosyl donor. More preferably, the saccharide, first saccharide and/or further saccharide is a protected glycosyl donor. Even more preferably, the saccharide, first saccharide and/or further saccharide is a glycosyl donor comprising a glycal, epoxide or orthoester group or having a leaving group at its reducing end selected from halogen, —O—C(=NH)—CCl₃, —O—C(=NPh)—CF₃, —OAc, —SR⁵, —SO-Ph, —SO₂-Ph, —O—(CH₂)₃—CH=CH₂, —O—P(OR⁵)₂, —O—PO(OR⁵)₂, —O—CO—OR⁵, —O—CO—SR⁵, —O—CS—SR⁵, —O—CS—OR⁵,

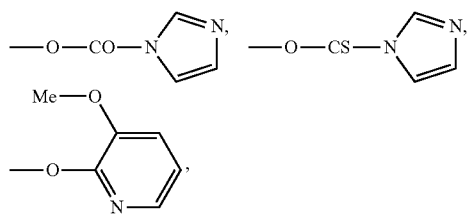

wherein R⁵ represents an alkyl or aryl group. Even more preferably, the saccharide, first saccharide and/or further saccharide is a glycosyl donor having a leaving group at its reducing end selected from halogen, —O—C(=NH)—CCl₃, —O—C(=NPh)—CF₃, —O—(CH₂)₃—CH=CH₂, —O—PO(OR⁵)₂, —OAc or —SR⁵, wherein R⁵ represents —CH₃, —CH₂CH₃, —CH₂CH₂CH₃, —(CH₂)₃CH₃, -Ph or -Tol. Even more preferably, the saccharide, first saccharide and/or further saccharide is a protected glycosyl donor having a leaving group at its reducing end selected from halogen, —O—C(=NH)—CCl₃, —O—C(=NPh)—CF₃, —O—(CH₂)₃—CH=CH₂, PO(OR⁵)₂, or —SR⁵, wherein R⁵ represents —CH₃, —CH₂CH₃, —CH₂CH₂CH₃, —(CH₂)₃CH₃, or -Tol.

Also, in steps B), B1), B2), B3), F1), and F2) of the inventive methods described herein, the saccharide, first saccharide and/or further saccharide is a saccharide building block consisting of a monosaccharide or disaccharide. Preferably, the saccharide, first saccharide and/or further saccharide is a glycosyl donor consisting of a monosaccharide or disaccharide. More preferably, the saccharide, first saccharide and/or further saccharide is a protected glycosyl donor consisting of a monosaccharide or disaccharide. Even more preferably, the saccharide, first saccharide and/or further saccharide is a monosaccharide or disaccharide glycosyl donor comprising a glycal, epoxide or orthoester group or having a leaving group at its reducing end selected from halogen, —O—C(=NH)—CCl₃, —O—C(=NPh)—CF₃, —OAc, —SR⁵, —SO-Ph, —SO₂-Ph, —O—(CH₂)₃—CH=CH₂, —O—P(OR⁵)₂, —O—PO(OR⁵)₂, —O—CO—OR⁵, —O—CO—SR⁵, —O—CS—SR⁵, —O—CS—OR⁵,

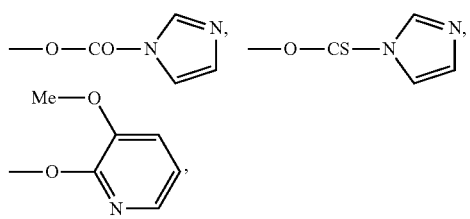

wherein R⁵ represents an alkyl or aryl group. Even more preferably, the saccharide, first saccharide and/or further saccharide is a monosaccharide or disaccharide glycosyl donor having a leaving group at its reducing end selected from halogen, —O—C(=NH)—CCl₃, —O—C(=NPh)—CF₃, —O—(CH₂)₃—CH=CH₂, —O—PO(OR⁵)₂, —OAc or —SR⁵, wherein R⁵ represents —CH₃, —CH₂CH₃, —CH₂CH₂CH₃, —(CH₂)₃CH₃, -Ph or -Tol. Even more preferably, the saccharide, first saccharide and/or further saccharide is a protected monosaccharide or disaccharide glycosyl donor having a leaving group at its reducing end selected from —O—C(=NH)—CCl₃, —O—C(=NPh)—CF₃, —O—(CH₂)₃—CH=CH₂, —O—PO(OR⁵)₂, or —SR⁵, wherein R⁵ represents —CH₃, —CH₂CH₃, —CH₂CH₂CH₃, —(CH₂)₃CH₃, or -Tol.

Also, in steps B), B1), B2), B3), F1), and F2) of the inventive methods described herein, the saccharide, first saccharide and/or further saccharide is a saccharide building block consisting of a monosaccharide. Preferably, the saccharide, first saccharide and/or further saccharide is a glycosyl donor consisting of a monosaccharide. More preferably, the saccharide, first saccharide and/or further saccharide is a protected glycosyl donor consisting of a monosaccharide. Even more preferably, the saccharide, first saccharide and/or further saccharide is a monosaccharide glycosyl donor comprising a glycal, epoxide or orthoester group or having a leaving group at its reducing end selected from halogen, —O—C(=NH)—CCl₃, —O—C(=NPh)—CF₃, —OAc, —SR⁵, —SO-Ph, —SO₂-Ph, —O—(CH₂)₃—CH=CH₂, —O—P(OR⁵)₂, —O—PO(OR⁵)₂, —O—CO—OR⁵, —O—CO—SR⁵, —O—CS—SR⁵, —O—CS—OR⁵,

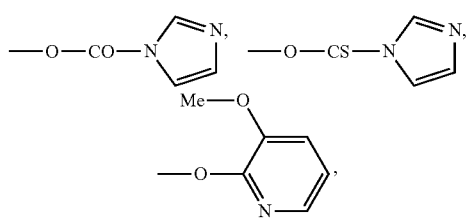

wherein $R^5$ represents an alkyl or aryl group. Even more preferably, the saccharide, first saccharide and/or further saccharide is a monosaccharide glycosyl donor having a leaving group at its reducing end selected from halogen, —O—C(=NH)—CCl$_3$, —O—C(=NPh)—CF$_3$, —O—(CH$_2$)$_3$—CH=CH$_2$, —O—PO(OR$^5$)$_2$, —OAc or —SR$^5$, wherein $R^5$ represents —CH$_3$, —CH$_2$CH$_3$, —CH$_2$CH$_2$CH$_3$, —(CH$_2$)$_3$CH$_3$, -Ph or -Tol.

Even more preferably, the saccharide, first saccharide and/or further saccharide is a protected monosaccharide glycosyl donor having a leaving group at its reducing end selected from halogen, —O—C(=NH)—CCl$_3$, —O—C(=NPh)—CF$_3$, —O—(CH$_2$)$_3$—CH=CH$_2$, —O—PO(OR$^5$)$_2$, or —SR$^5$, wherein $R^5$ represents —CH$_3$, —CH$_2$CH$_3$, —CH$_2$CH$_2$CH$_3$, —(CH$_2$)$_3$CH$_3$, or -Tol.

In steps D), D1), D2), H1), H2), and H3) of the inventive methods described herein, the vapor of a solvent and a glycosylation agent is preferably applied to a solid support having a temperature below 5° C., more preferably below 0° C., more preferably between −78° C. and 0° C., more preferably between −30° C. and 0° C., more preferably between −20° C. and 0° C. and more preferably between −20° C. and +5° C.

In steps D), D1), D2), H1), H2), and H3) of the inventive methods described herein, the ratio of the solvent and the glycosylation reagent in the vapor is preferably in the range of 1:10 to 100,000:1, more preferably in the range of 1:1 to 100,000:1, more preferably in the range of 2:1 to 100,000:1, more preferably in the range of 5:1 to 100,000:1, and most preferably in the range of 10:1 to 100,000:1.

The vapor mixture is preferably prepared from a solution or a mixture of a glycosylation reagent in an aprotic organic solvent wherein the ratio of the solvent and the glycosylation reagent in the solution or mixture (i.e. bulk) is preferably in the range of 10:10 to 1,000,000:1, more preferably in the range of 10:1 to 1,000,000:1, more preferably in the range of 20:1 to 1,000,000:1, more preferably in the range of 50:1 to 1,000,000:1, and most preferably in the range of 100:1 to 1,000,000:1.

In one embodiment, the vapor mixture of the solvent and the glycosylation reagent is applied in laminar flow onto the solid support in order to achieve convective condensation of the vapor mixture and to avoid diffusion of the discrete locations or spots on the solid support.

In one embodiment, an additional reagent for the glycosylation reaction is delivered together with the first saccharide onto the solid support. Thus, one aspect of the present invention is directed to a method for synthesizing saccharides comprising the steps:

A1) providing a solid support with acceptor groups for reacting with a saccharide,
B1) delivering a first saccharide and an additional reagent onto the solid support;
C1) drying the solid support,
D1) applying a vapor of a solution of a glycosylation reagent in a solvent onto the solid support at a temperature below 20° C. in order to initiate a coupling reaction of the first saccharide to the acceptor group of the solid support in order to obtain a saccharide immobilized to the solid support,
E1) washing and drying the solid support,
F1) delivering a further saccharide onto the solid support;
G1) drying the solid support,
H1) applying a vapor of a solution of a glycosylation reagent in a solvent onto the solid support at a temperature below 20° C. in order to initiate the coupling reaction of the further saccharide to the saccharide immobilized to the solid support,
I1) washing and drying the solid support,
J1) repeating the steps F1) to I1) until the saccharide of desired length is obtained.

Preferably, the additional reagent is N-iodosuccinimide.

In steps D), D1), D2), H1), H2), and H3) of the inventive methods described herein, the solvent in the vapor is preferably an aprotic organic solvent. Preferably, the solvent is selected from methylene chloride, acetonitrile, chloroform, diethyl ether, 1,4-dioxane, methyl tert-butyl ether, toluene and ethyl acetate.

In steps D), D1), D2), H1), H2), and H3) of the inventive methods described herein the glycosylation reagent is preferably a Brønsted acid or Lewis acid. More preferably, the glycosylation reagent is a Lewis acid. More preferably, the glycosylation reagent is selected from: AgOTf, BF$_3$·OEt$_2$, trimethylsilyl trifluoromethanesulfonate (TMSOTf), trifluoromethanesulfonic acid (TfOH), trifluoromethanesulfonic anhydride (Tf$_2$O, triflic anhydride), lanthanoid(III) triflates, NIS/AgOTf, NIS/TfOH or dimethyl(methylthio)sulfonium trifluoromethanesulfonate (DMTST). More preferably, the glycosylation reagent is selected from: trimethylsilyl trifluoromethanesulfonate (TMSOTf), trifluoromethanesulfonic acid (TfOH), trifluoromethanesulfonic anhydride (Tf$_2$O, triflic anhydride), and NIS/TfOH. Most preferably, the glycosylation reagent is selected from: trimethylsilyl trifluoromethanesulfonate (TMSOTf), trifluoromethanesulfonic acid (TfOH), trifluoromethanesulfonic anhydride (Tf$_2$O, triflic anhydride), and NIS/TfOH.

The washing steps E1), E2), I1) and I2) of the inventive methods described herein may be carried out in the presence of a base, preferably an amine base in order to prevent decomposition or cleavage of the saccharide from the solid support.

E1)/E2)/I1)/I2) washing the solid support in the presence of a base, preferably an amine, and drying the solid support In case the saccharides employed in the inventive method described herein are protected saccharides, the inventive method can further comprise a step of deprotecting the saccharide after steps C), J1) or J2), K) performing removal of protecting groups from the saccharide.

The protecting groups are defined herein, preferably said protecting groups are protecting groups for hydroxyl groups and/or protecting groups for amine groups.

Preferred protecting groups for hydroxyl groups are acetyl, phenyl, benzyl, isopropylidene, benzylidene, benzoyl, p-methoxybenzyl, p-methoxybenzylidene, p-methoxyphenyl, p-bromobenzylidene, p-nitrophenyl, allyl, allyloxycarbonyl, monochloroacetyl, isopropyl, p-bromobenzyl, dimethoxytrityl, trityl, 2-naphthylmethyl, pivaloyl, triisopropylsilyl, tert-butyldimethylsilyl, tert-butyldiphenylsilyl, tert-butylmethoxyphenylsilyl, triethylsilyl, trimethylsilyl, 2-trimethylsilylethoxymethyl, 9-fluorenylmethoxycarbonyl, tert-butyloxycarbonyl, benzyloxymethyl, methyloxymethyl, tert-butyloxymethyl, methoxyethyloxymethyl, and levulinoyl.

Preferred protecting groups for amine groups are acetyl, benzyl, p-methoxyphenyl, benzoyl, p-methoxybenzyl, 3,4-dimethoxybenzyl, benzyloxycarbonyl(Cbz), allyloxycarbonyl, trichloroacetyl (TCA), trifluoroacetyl, trichloroethyl (Troc), p-bromobenzyl, dimethoxytrityl, trityl, 2-naphthylmethyl, pivaloyl, 9-fluorenylmethoxycarbonyl (Fmoc), tert-butyloxycarbonyl(BOC), levulinoyl, tosyl, nosyl, 2-nitrophenylsulfenyl (Nps), and phthalimidyl.

Thus, in one embodiment of the present invention the method for synthesizing saccharides comprises the steps:
- A1) providing a solid support with acceptor groups for reacting with a saccharide,
- B1) delivering a first saccharide onto the solid support;
- C1) drying the solid support,
- D1) applying a vapor of a solution of a glycosylation reagent in a solvent onto the solid support at a temperature below 20° C. in order to initiate a coupling reaction of the first saccharide to the acceptor group of the solid support in order to obtain a saccharide immobilized to the solid support,
- E1) washing and drying the solid support,
- F1) delivering a further saccharide onto the solid support;
- G1) drying the solid support,
- H1) applying a vapor of a solution of a glycosylation reagent in a solvent onto the solid support at a temperature below 20° C. in order to initiate the coupling reaction of the further saccharide to the saccharide immobilized to the solid support,
- I1) washing and drying the solid support,
- J1) repeating the steps F1) to I1) until the saccharide of desired length is obtained;
- K) performing removal of protecting groups from the saccharide.

In another embodiment of the present invention the method for synthesizing saccharides comprises the steps:
- A1) providing a solid support with acceptor groups for reacting with a saccharide,
- B1) delivering a first saccharide onto the solid support;
- C1) drying the solid support,
- D1) applying a vapor of a solution of a glycosylation reagent in a solvent onto the solid support at a temperature below 20° C. in order to initiate a coupling reaction of the first saccharide to the acceptor group of the solid support in order to obtain a saccharide immobilized to the solid support,
- E1) washing and drying the solid support,
- F1) delivering a further saccharide onto the solid support;
- G1) drying the solid support,
- H1) applying a vapor of a solution of a glycosylation reagent in a solvent onto the solid support at a temperature below 20° C. in order to initiate the coupling reaction of the further saccharide to the saccharide immobilized to the solid support,
- I1) washing and drying the solid support,
- J1) repeating the steps F1) to I1) until the saccharide of desired length is obtained;
- K) performing removal of protecting groups from the saccharide;
- L) cleaving the saccharide from the solid support; and
- M) optionally purifying the saccharide obtained from step L).

In another embodiment of the present invention the method for synthesizing saccharides comprises the steps:
- A1) providing a solid support with acceptor groups for reacting with a saccharide,
- B1) applying a solution of a first saccharide onto the solid support;
- C1) drying the solid support and evaporating the solvent under reduced pressure and/or heating,
- D1) applying a vapor of a solution of a glycosylation reagent in a solvent onto the solid support at a temperature below 20° C. in order to initiate a coupling reaction of the first saccharide to the acceptor group of the solid support in order to obtain a saccharide immobilized to the solid support,
- E1) washing and drying the solid support,
- F1) applying a solution of a further saccharide onto the solid support;
- G1) drying the solid support and evaporating the solvent under reduced pressure and/or heating,
- H1) applying a vapor of a solution of a glycosylation reagent in a solvent onto the solid support at a temperature below 20° C. in order to initiate the coupling reaction of the further saccharide to the saccharide immobilized to the solid support,
- I1) washing and drying the solid support,
- J1) repeating the steps F1) to I1) until the saccharide of desired length is obtained;
- K) performing removal of protecting groups from the saccharide;
- L) cleaving the saccharide from the solid support; and
- M) optionally purifying the saccharide obtained from step L).

Saccharide Array

Another aspect of the present invention is directed to the parallelized synthesis of saccharides on a solid support. According to the present invention, the saccharide building blocks, which are unreactive, are delivered first on the solid support and subsequently the coupling reaction is carried out by exposing the saccharide building blocks to a vapor comprising a solvent and a glycosylation reagent at low temperatures. The vapor condenses on the solid support and initiates the coupling reaction, thereby allowing the simultaneous synthesis of different saccharides at discrete locations on the solid support.

Thus, the present invention is also directed to a method for producing saccharide arrays comprising the steps of
- A) providing a solid support having a plurality of acceptor groups for reacting with a saccharide at discrete locations immobilized thereto;
- B) delivering at least one saccharide at the discrete locations on the surface of the solid support;
- C) applying a vapor of a solution of a glycosylation reagent in a solvent onto the solid support at a temperature below 20° C. in order to initiate a coupling reaction of the at least one saccharide to the plurality of acceptor groups immobilized at discrete locations to the solid support.

In one embodiment, the method for producing saccharide arrays comprises the steps of
- A) providing a solid support having a plurality of acceptor groups for reacting with a saccharide at discrete locations immobilized thereto;
- B) delivering at least one saccharide at the discrete locations on the surface of the solid support;
- C') drying the solid support obtained in step B) under reduced pressure and/or heating;
- C) applying a vapor of a solution of a glycosylation reagent in a solvent onto the solid support at a temperature below 20° C. in order to initiate a coupling reaction of the at least one saccharide to the plurality of acceptor groups immobilized at discrete locations to the solid support.

In one embodiment, the method for producing saccharide arrays comprises the steps of
- A) providing a solid support having a plurality of acceptor groups for reacting with a saccharide at discrete locations immobilized thereto;
- B) applying at least one solution of a saccharide at the discrete locations on the surface of the solid support;

C') drying the solid support obtained in step B) and evaporating the solvent of the at least one solution under reduced pressure and/or heating;

C) applying a vapor of a solution of a glycosylation reagent in a solvent onto the solid support at a temperature below 20° C. in order to initiate a coupling reaction of the at least one saccharide to the plurality of acceptor groups immobilized at discrete locations to the solid support.

In one embodiment, the method for producing saccharide arrays comprises the steps of
A) providing a solid support having a plurality of acceptor groups for reacting with a saccharide at discrete locations immobilized thereto;
B) delivering at least one saccharide at the discrete locations on the surface of the solid support;
C') drying the solid support obtained in step B) under reduced pressure and/or heating;
C) applying a vapor of a solution of a glycosylation reagent in a solvent onto the solid support at a temperature below 20° C. in order to initiate a coupling reaction of the at least one saccharide to the plurality of acceptor groups immobilized at discrete locations to the solid support;
K) performing removal of protecting groups from the saccharide obtained in step C).

In one embodiment, the method for producing saccharide arrays comprises the steps of
A) providing a solid support having a plurality of acceptor groups for reacting with a saccharide at discrete locations immobilized thereto;
B) delivering at least one saccharide at the discrete locations on the surface of the solid support;
C) applying a vapor of a solution of a glycosylation reagent in a solvent onto the solid support at a temperature below 5° C., more preferably below 0° C., more preferably between −78° C. and 0° C. and most preferably between −20° C. and 0° C. in order to initiate a coupling reaction of the at least one saccharide to the plurality of acceptor groups immobilized at discrete locations to the solid support.

In one embodiment, the method for producing saccharide arrays comprises the steps of
A) providing a solid support having a plurality of acceptor groups for reacting with a saccharide at discrete locations immobilized thereto;
B) delivering at least one saccharide at the discrete locations on the surface of the solid support;
C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support,
wherein the ratio of the solvent and the glycosylation reagent in the vapor is in the range of 1:10 to 100,000:1.

In one embodiment, the method for producing saccharide arrays comprises the steps of
A) providing a solid support having a plurality of acceptor groups for reacting with a saccharide at discrete locations immobilized thereto;
B) delivering at least one saccharide at the discrete locations on the surface of the solid support;
C) applying a vapor of a solution of a glycosylation reagent in a solvent onto the solid support at a temperature below 20° C. in order to initiate a coupling reaction of the at least one saccharide to the plurality of acceptor groups immobilized at discrete locations to the solid support,
wherein the solvent is an aprotic organic solvent selected from: methylene chloride, acetonitrile, chloroform, diethyl ether, 1,4-dioxane, methyl tert-butyl ether, toluene and ethyl acetate.

In one embodiment, the method for producing saccharide arrays comprises the steps of
A) providing a solid support having a plurality of acceptor groups for reacting with a saccharide at discrete locations immobilized thereto;
B) delivering at least one saccharide at the discrete locations on the surface of the solid support;
C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support,
wherein the glycosylation reagent is a Lewis acid selected from: AgOTf, $BF_3 \cdot OEt_2$, trimethylsilyl trifluoromethanesulfonate (TMSOTf), trifluoromethanesulfonic acid (TfOH), trifluoromethanesulfonic anhydride ($Tf_2O$, triflic anhydride), lanthanoid(III) triflates, NIS/AgOTf, NIS/TfOH or dimethyl(methylthio)sulfonium trifluoromethanesulfonate (DMTST), preferably trimethylsilyl trifluoromethanesulfonate (TMSOTf), trifluoromethanesulfonic acid (TfOH), trifluoromethanesulfonic anhydride, or NIS/TfOH.

In one embodiment, the method for producing saccharide arrays comprises the steps of
A) providing a solid support having a plurality of acceptor groups for reacting with a saccharide at discrete locations immobilized thereto;
B) delivering at least one saccharide at the discrete locations on the surface of the solid support;
C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support,
wherein the at least one saccharide is a protected glycosyl donor comprising a glycal, epoxide or orthoester group or having a leaving group at the reducing end selected from halogen, —O—C(=NH)—$CCl_3$, —O—C(=NPh)—$CF_3$, —OAc, —$SR^5$, —SO-Ph, —$SO_2$-Ph, —O—$(CH_2)_3$—CH=$CH_2$, —O—P$(OR^5)_2$, —O—PO$(OR^5)_2$, —O—CO—$OR^5$, —O—CO—$SR^5$, —O—CS—$SR^5$, —O—CS—$OR^5$,

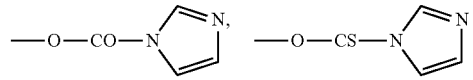

or

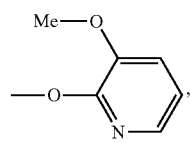

wherein $R^5$ represents an alkyl or aryl group.

In one embodiment, the method for producing saccharide arrays comprises the steps of
  A) providing a solid support having a plurality of acceptor groups for reacting with a saccharide at discrete locations immobilized thereto;
  B) delivering at least one saccharide at the discrete locations on the surface of the solid support;
  C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support,
wherein the at least one saccharide is a protected glycosyl donor having a leaving group at the reducing end selected from halogen, —O—C(=NH)—CCl$_3$, —O—C(=NPh)—CF$_3$, —O—(CH$_2$)$_3$—CH=CH$_2$, —O—PO(OR$^5$)$_2$, or —SR$^5$, wherein R$^5$ represents —CH$_3$, —CH$_2$CH$_3$, —CH$_2$CH$_2$CH$_3$, —(CH$_2$)$_3$CH$_3$, or -Tol.

In one embodiment, the method for producing saccharide arrays comprises the steps of
  A) providing a solid support having a plurality of acceptor groups for reacting with a saccharide at discrete locations immobilized thereto;
  B) delivering at least one monosaccharide at the discrete locations on the surface of the solid support;
  C) applying a vapor of a solution of a glycosylation reagent in a solvent onto the solid support at a temperature below 20° C., in order to initiate a coupling reaction of the at least one monosaccharide to the plurality of acceptor groups immobilized at discrete locations to the solid support,
wherein the at least one monosaccharide is a protected monosaccharide glycosyl donor having a leaving group at the reducing end selected from halogen, —O—C(=NH)—CCl$_3$, —O—C(=NPh)—CF$_3$, —O—(CH$_2$)$_3$—CH=CH$_2$, —O—PO(OR$^5$)$_2$, or —SR$^5$, wherein R$^5$ represents —CH$_3$, —CH$_2$CH$_3$, —CH$_2$CH$_2$CH$_3$, —(CH$_2$)$_3$CH$_3$, or -Tol.

In one embodiment, the method for producing saccharide arrays comprises the steps of
  A) providing a solid support having a plurality of acceptor groups for reacting with a saccharide at discrete locations immobilized thereto;
  B) delivering at least one saccharide at the discrete locations on the surface of the solid support;
  C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support,
wherein in step B) the at least one saccharide is delivered as a solid, from a solution or in a polymer matrix onto the solid support.

In one embodiment, the method for producing saccharide arrays comprises the steps of
  A) providing a solid support having a plurality of acceptor groups for reacting with a saccharide at discrete locations immobilized thereto;
  B) delivering a solution of at least one saccharide at the discrete locations on the surface of the solid support;
  C') drying the solid support obtained in step B) under reduced pressure and/or heating;
  C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support.

In one embodiment, the method for producing saccharide arrays comprises the steps of
  A) providing a solid support having a plurality of acceptor groups for reacting with a saccharide at discrete spots immobilized thereto;
  B) delivering a solution of at least one saccharide at the discrete spots on the surface of the solid support;
  C') drying the solid support obtained in step B) under reduced pressure and/or heating;
  C) applying a vapor of a solution of a glycosylation reagent in a solvent onto the solid support at a temperature below 20° C., in order to initiate a coupling reaction of the at least one saccharide to the plurality of acceptor groups immobilized at discrete spots to the solid support.

In one embodiment, the method for producing saccharide arrays comprises the steps of
  A) providing a solid support having a plurality of acceptor groups for reacting with a saccharide at discrete spots immobilized thereto;
  B) delivering a solution of at least one saccharide at the discrete spots on the surface of the solid support;
  C') drying the solid support obtained in step B) under reduced pressure and/or heating;
  C) applying a vapor of a solution of a glycosylation reagent in a solvent onto the solid support at a temperature below 5° C., in order to initiate a coupling reaction of the at least one saccharide to the plurality of acceptor groups immobilized at discrete spots to the solid support.

In one embodiment, the method for producing saccharide arrays comprises the steps of
  A) providing a solid support having a plurality of acceptor groups for reacting with a saccharide at discrete spots immobilized thereto;
  B) delivering a solution of at least one saccharide at the discrete spots on the surface of the solid support;
  C') drying the solid support obtained in step B) under reduced pressure and/or heating;
  C) applying a vapor of a solution of a glycosylation reagent in a solvent onto the solid support at a temperature below 5° C., in order to initiate a coupling reaction of the at least one saccharide to the plurality of acceptor groups immobilized at discrete spots to the solid support.

In one embodiment, the method for producing saccharide arrays comprises the steps of
  A) providing a solid support having a plurality of acceptor groups for reacting with a saccharide at discrete spots covalently attached thereto;
  B) delivering a solution of at least one saccharide at the discrete spots on the surface of the solid support;
  C') drying the solid support obtained in step B) under reduced pressure and/or heating;
  C) applying a vapor of a solution of a glycosylation reagent in a solvent onto the solid support at a temperature below 5° C., in order to initiate a coupling reaction of the at least one saccharide to the plurality of acceptor groups covalently attached at discrete spots to the solid support,
wherein the solid support is a cellulose membrane with acceptor groups comprising glycosyl acceptors as defined herein.

In one embodiment, the method for producing saccharide arrays comprises the steps of
- A) providing a solid support having a plurality of acceptor groups for reacting with a saccharide at discrete spots covalently attached thereto;
- B) delivering a solution of at least one saccharide at the discrete spots on the surface of the solid support;
- C') drying the solid support obtained in step B) under reduced pressure and/or heating;
- C) applying a vapor of a solution of a glycosylation reagent in a solvent onto the solid support at a temperature below 5° C., in order to initiate a coupling reaction of the at least one saccharide to the plurality of acceptor groups covalently attached at discrete spots to the solid support, wherein the solid support is a cellulose membrane.

In one embodiment, the method for producing saccharide arrays comprises the steps of
- A) providing a solid support having a plurality of acceptor groups for reacting with a saccharide at discrete spots covalently attached thereto;
- B) delivering a solution of at least one saccharide at the discrete spots on the surface of the solid support;
- C') drying the solid support obtained in step B) under reduced pressure and/or heating;
- C) applying a vapor of a solution of a glycosylation reagent in a solvent onto the solid support at a temperature below 5° C., in order to initiate a coupling reaction of the at least one saccharide to the plurality of acceptor groups covalently attached at discrete spots to the solid support,
- K) performing removal of protecting groups from the saccharide obtained in step C), wherein the solid support is a cellulose membrane and wherein the at least one saccharide is a protected glycosyl donor having a leaving group at the reducing end selected from halogen, —O—C(=NH)—CCl$_3$, —O—C(=NPh)—CF$_3$, —O—(CH$_2$)$_3$—CH=CH$_2$, —O—PO(OR$^5$)$_2$, or —SR$^5$, wherein R$^5$ represents —CH$_3$, —CH$_2$CH$_3$, —CH$_2$CH$_2$CH$_3$, —(CH$_2$)$_3$CH$_3$, or -Tol.

In one embodiment, the method for producing saccharide arrays comprises the steps of
- A) providing a solid support having a plurality of acceptor groups for reacting with a saccharide at discrete spots covalently attached thereto;
- B) delivering a solution of at least one saccharide at the discrete spots on the surface of the solid support;
- C') drying the solid support obtained in step B) under reduced pressure and/or heating;
- C) applying a vapor of a solution of a glycosylation reagent in a solvent onto the solid support at a temperature below 5° C., in order to initiate a coupling reaction of the at least one saccharide to the plurality of acceptor groups covalently attached at discrete spots to the solid support,
- K) performing removal of protecting groups from the saccharide obtained in step C),
- L) cleaving the at least one saccharide from the solid support; and
- M) optionally purifying the saccharide obtained from step L), wherein the solid support is a cellulose membrane and wherein the at least one saccharide is a protected glycosyl donor having a leaving group at the reducing end selected from halogen, —O—C(=NH)—CCl$_3$, —O—C(=NPh)—CF$_3$, —O—(CH$_2$)$_3$—CH=CH$_2$, —O—PO(OR$^5$)$_2$, or —SR$^5$, wherein R$^5$ represents —CH$_3$, —CH$_2$CH$_3$, —CH$_2$CH$_2$CH$_3$, —(CH$_2$)$_3$CH$_3$, or -Tol.

In one embodiment, the method for producing saccharide arrays comprises the steps of
- A2) providing a solid support having acceptor groups for covalently attaching a saccharide at discrete spots;
- B2) delivering a solution of a first saccharide at the discrete spots on the surface of the solid support;
- C2') drying the solid support;
- D2) applying a vapor of a solution of a glycosylation reagent in a solvent onto the solid support at a temperature below 20° C. in order to initiate a coupling reaction of the first saccharide to the acceptor group of the solid support in order to obtain a saccharide covalently attached at discrete spots on the solid support,
- E2) washing and drying the solid support,
- F2) delivering a solution of at least one further saccharide at the discrete spots on the surface of the solid support;
- G2) drying the solid support,
- H2) applying a vapor of a solution of a glycosylation reagent in a solvent onto the solid support at a temperature below 5° C., in order to initiate a coupling reaction of the at least one further saccharide to the saccharides covalently attached at discrete spots to the solid support,
- I2) washing and drying the solid support,
- J2) repeating the steps F2) to 12) until the saccharide of desired length is obtained;
- K2) performing removal of protecting groups from the saccharide obtained in step J2),
- L2) cleaving the at least one saccharide from the solid support; and
- M2) optionally purifying the at least one saccharide obtained from step L2), wherein the solid support is a cellulose membrane and wherein the first saccharide and/or at least one further saccharide is a protected glycosyl donor having a leaving group at the reducing end selected from halogen, —O—C(=NH)—CCl$_3$, —O—C(=NPh)—CF$_3$, —O—(CH$_2$)$_3$—CH=CH$_2$, —O—PO(OR$^5$)$_2$, or —SR$^5$, wherein R$^5$ represents —CH$_3$, —CH$_2$CH$_3$, —CH$_2$CH$_2$CH$_3$, —(CH$_2$)$_3$CH$_3$, or -Tol.

In one embodiment, the method for producing saccharide arrays comprises the steps of
- A2) providing a solid support having acceptor groups for covalently attaching a saccharide at discrete spots;
- B2) delivering a solution of a first monosaccharide at the discrete spots on the surface of the solid support;
- C2') drying the solid support;
- D2) applying a vapor of a solution of a glycosylation reagent in a solvent onto the solid support at a temperature below 20° C. in order to initiate a coupling reaction of the first monosaccharide to the acceptor group of the solid support in order to obtain a monosaccharide covalently attached at discrete spots on the solid support,
- E2) washing and drying the solid support,
- F2) delivering a solution of at least one further monosaccharide at the discrete spots on the surface of the solid support;
- G2) drying the solid support,
- H2) applying a vapor of a solution of a glycosylation reagent in a solvent onto the solid support at a temperature below 5° C., in order to initiate a coupling reaction of the at least one further monosaccharide to the monosaccharides covalently attached at discrete spots to the solid support, I2) washing and drying the solid support, J2) repeating the steps F2) to I2) until the saccharide of desired length is obtained;

K2) performing removal of protecting groups from the saccharide obtained in step J2), L2) cleaving the at least one saccharide from the solid support; and M2) optionally purifying the at least one saccharide obtained from step L2), wherein the solid support is a cellulose membrane and wherein first monosaccharide and/or the at least one further monosaccharide is a protected monosaccharide glycosyl donor having a leaving group at the reducing end selected from halogen, $-O-C(=NH)-CCl_3$, $-O-C(=NPh)-CF_3$, $-O-(CH_2)_3-CH=CH_2$, $-O-PO(OR^5)_2$, or $-SR^5$, wherein $R^5$ represents $-CH_3$, $-CH_2CH_3$, $-CH_2CH_2CH_3$, $-(CH_2)_3CH_3$, or -Tol.

High-Density Saccharide Array

Another aspect of the present invention is directed to the provision of high-density saccharide arrays. The inventors found out that under coupling reaction conditions of the inventive method the delivered saccharide building blocks do not migrate or dissipate on the solid support, thereby a high-density pattern or array of the delivered saccharides is maintained, which renders the present invention particularly useful for the provision of saccharide arrays, particularly high-density saccharide arrays having a pitch of less than 300 µm.

Thus, the present invention is also directed to a method for producing high-density saccharide arrays, comprising the steps of:

A3) providing a solid support with a plurality of acceptor groups immobilized at discrete spots for reacting with a saccharide, and A3') providing a donor support comprising a film layer, in which at least one saccharide is present, and an intermediate layer between the support and the film layer, B3) selectively transferring of material of the at least one saccharide from the donor support to the solid support of step A3) and site-specific fixing of the transferred material to the discrete spots of the solid support by electromagnetic irradiation comprising laser light;

C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form.

In one embodiment, the method for producing high-density saccharide arrays comprises the steps of:

A3) providing a solid support with acceptor groups immobilized at discrete spots for reacting with a saccharide, and A3') providing a donor support comprising a film layer, in which at least one saccharide is present, and an intermediate layer between the support and the film layer, B3) selectively transferring of material of the at least one saccharide from the donor support to the solid support of step A3) and site-specific fixing of the transferred material to the discrete spots of the solid support by electromagnetic irradiation comprising laser light;

C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form; and wherein the acceptor groups comprises a saccharide, preferably glycosyl acceptor, suitable for reacting with a saccharide as defined herein.

In one embodiment, the method for producing high-density saccharide arrays comprises the steps of:

A3) providing a solid support with acceptor groups immobilized at discrete spots for reacting with a saccharide, and A3') providing a donor support comprising a film layer, in which at least one saccharide is present, and an intermediate layer between the support and the film layer, B3) selectively transferring of material of the at least one saccharide from the donor support to the solid support of step A3) and site-specific fixing of the transferred material to the discrete spots of the solid support by electromagnetic irradiation comprising laser light;

C3') drying the solid support obtained in step B3) under reduced pressure and/or heating;

C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form.

In one embodiment, the method for producing high-density saccharide arrays comprises the steps of:

A3) providing a solid support with acceptor groups immobilized at discrete spots for reacting with a saccharide, and A3') providing a donor support comprising a film layer, in which at least one saccharide is present, and an intermediate layer between the support and the film layer, B3) selectively transferring of material of the at least one saccharide from the donor support to the solid support of step A3) and site-specific fixing of the transferred material to the discrete spots of the solid support by electromagnetic irradiation comprising laser light;

C3') drying the solid support obtained in step B3) under reduced pressure and/or heating;

C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, K3) performing removal of protecting groups from the saccharide obtained in step $C_3$), wherein the selective transfer and the site-specific fixing of the at least one saccharide molecule from the donor support to the solid support is without direct contact between the supports and the at least one saccharide molecule is transferred in liquid or gaseous form.

In one embodiment, the method for producing high-density saccharide arrays comprises the steps of:
- A3) providing a solid support with acceptor groups immobilized at discrete spots for reacting with a saccharide, and
- A3') providing a donor support comprising a film layer, in which at least one saccharide is present, and an intermediate layer between the support and the film layer,
- B3) selectively transferring of material of the at least one saccharide from the donor support to the solid support of step A3) and site-specific fixing of the transferred material to the discrete spots of the solid support by electromagnetic irradiation comprising laser light;
- C3) applying a vapor of a solution of a glycosylation reagent in a solvent onto the solid support at a temperature below 5° C., more preferably below 0° C., more preferably between −78° C. and 0° C. and most preferably between −20° C. and 0° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form.

In one embodiment, the method for producing high-density saccharide arrays comprises the steps of:
- A3) providing a solid support with acceptor groups immobilized at discrete spots for reacting with a saccharide, and
- A3') providing a donor support comprising a film layer, in which at least one saccharide is present, and an intermediate layer between the support and the film layer,
- B3) selectively transferring of material of the at least one saccharide from the donor support to the solid support of step A3) and site-specific fixing of the transferred material to the discrete spots of the solid support by electromagnetic irradiation comprising laser light;
- C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form, and
wherein the ratio of the solvent and the glycosylation reagent in the vapor is in the range of 1:10 to 100,000:1.

In one embodiment, the method for producing high-density saccharide arrays comprises the steps of:
- A3) providing a solid support with acceptor groups immobilized at discrete spots for reacting with a saccharide, and
- A3') providing a donor support comprising a film layer, in which at least one saccharide is present, and an intermediate layer between the support and the film layer,
- B3) selectively transferring of material of the at least one saccharide from the donor support to the solid support of step A3) and site-specific fixing of the transferred material to the discrete spots of the solid support by electromagnetic irradiation comprising laser light;
- C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form, and
wherein the solvent is an aprotic organic solvent selected from: methylene chloride, acetonitrile, chloroform, diethyl ether, 1,4-dioxane, methyl tert-butyl ether, toluene and ethyl acetate.

In one embodiment, the method for producing high-density saccharide arrays comprises the steps of:
- A3) providing a solid support with acceptor groups immobilized at discrete spots for reacting with a saccharide, and
- A3') providing a donor support comprising a film layer, in which at least one saccharide is present, and an intermediate layer between the support and the film layer,
- B3) selectively transferring of material of the at least one saccharide from the donor support to the solid support of step A3) and site-specific fixing of the transferred material to the discrete spots of the solid support by electromagnetic irradiation comprising laser light;
- C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form, and
wherein the solvent is an aprotic organic solvent selected from: methylene chloride, acetonitrile, chloroform, diethyl ether, 1,4-dioxane, methyl tert-butyl ether, toluene and ethyl acetate.

In one embodiment, the method for producing high-density saccharide arrays comprises the steps of:
- A3) providing a solid support with acceptor groups immobilized at discrete spots for reacting with a saccharide, and
- A3') providing a donor support comprising a film layer, in which at least one saccharide is present, and an intermediate layer between the support and the film layer,
- B3) selectively transferring of material of the at least one saccharide from the donor support to the solid support of step A3) and site-specific fixing of the transferred material to the discrete spots of the solid support by electromagnetic irradiation comprising laser light;
- C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form, and wherein the glycosylation reagent is a Lewis acid selected from: AgOTf, $BF_3 \cdot OEt_2$, trimethylsilyl trifluoromethanesulfonate (TMSOTf), trifluoromethanesulfonic acid (TfOH), trifluoromethanesulfonic anhydride ($Tf_2O$, triflic anhydride), lanthanoid(III) triflates, NIS/AgOTf, NIS/TfOH or dimethyl(methylthio)sulfonium trifluoromethanesulfonate (DMTST), preferably trimethylsilyl trifluoromethanesulfonate (TMSOTf), trifluoromethanesulfonic acid (TfOH), trifluoromethanesulfonic anhydride, or NIS/TfOH.

In one embodiment, the method for producing high-density saccharide arrays comprises the steps of:
A3) providing a solid support with acceptor groups immobilized at discrete spots for reacting with a saccharide, and
A3') providing a donor support comprising a film layer, in which at least one saccharide is present, and an intermediate layer between the support and the film layer,
B3) selectively transferring of material of the at least one saccharide from the donor support to the solid support of step A3) and site-specific fixing of the transferred material to the discrete spots of the solid support by electromagnetic irradiation comprising laser light;
C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form, and wherein the at least one further saccharide is a protected glycosyl donor comprising a glycal, epoxide or orthoester group or having a leaving group at the reducing end selected from halogen, —O—C(=NH)—$CCl_3$, —O—C(=NPh)—$CF_3$, —OAc, —$SR^5$, —SO-Ph, —$SO_2$-Ph, —O—$(CH_2)_3$—CH=$CF_{12}$, —O—$P(OR^5)_2$, —O—$PO(OR^5)_2$, —O—CO—$OR^5$, —O—CO—$SR^5$, —O—CS—$SR^5$, —O—CS—$OR^5$,

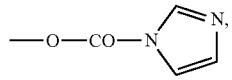

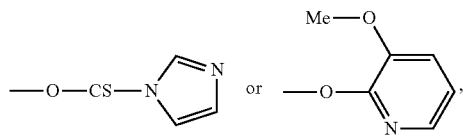

wherein $R^5$ represents an alkyl or aryl group.

In one embodiment, the method for producing high-density saccharide arrays comprises the steps of:
A3) providing a solid support with acceptor groups immobilized at discrete spots for reacting with a saccharide, and
A3') providing a donor support comprising a film layer, in which at least one saccharide is present, and an intermediate layer between the support and the film layer,
B3) selectively transferring of material of the at least one saccharide from the donor support to the solid support of step A3) and site-specific fixing of the transferred material to the discrete spots of the solid support by electromagnetic irradiation comprising laser light;
C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form, and wherein the at least one further saccharide is a protected glycosyl donor having a leaving group at the reducing end selected from halogen, —O—C(=NH)—$CCl_3$, —O—C(=NPh)—$CF_3$, —O—$(CH_2)_3$—CH=$CH_2$, —O—PO$(OR^5)_2$, or —$SR^5$, wherein $R^5$ represents —$CH_3$, —$CH_2CH_3$, —$CH_2CH_2CH_3$, —$(CH_2)_3CH_3$, or -Tol.

In one embodiment, the method for producing high-density saccharide arrays comprises the steps of:
A3) providing a solid support with acceptor groups immobilized at discrete spots for reacting with a saccharide, and
A3') providing a donor support comprising a film layer, in which at least one saccharide is present, and an intermediate layer between the support and the film layer,
B3) selectively transferring of material of the at least one saccharide from the donor support to the solid support of step A3) and site-specific fixing of the transferred material to the discrete spots of the solid support by electromagnetic irradiation comprising laser light;
C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form, and wherein the intermediate layer comprises polyimide, polycaprolactone, polystyrene or polyethylene.

In one embodiment, the method for producing high-density saccharide arrays comprises the steps of:
A3) providing a solid support with acceptor groups immobilized at discrete spots for reacting with a saccharide, and
A3') providing a donor support comprising a film layer, in which at least one saccharide is present, and an intermediate layer between the support and the film layer,
B3) selectively transferring of material of the at least one saccharide from the donor support to the solid support of step A3) and site-specific fixing of the transferred material to the discrete spots of the solid support by electromagnetic irradiation comprising laser light;
C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form, and wherein the intermediate layer comprises polyimide, polycaprolactone, polystyrene or polyethylene.

Preferably, in step B3) the laser light is applied with a power output between 50 mW to 150 mW, preferably between 75 mW to 125 mW, most preferably 100 mW.

Preferably, the focus diameter of the laser light in step B3) is in the range of 5 µm to 70 µm, preferably between 10 µm to 50 µm, most preferably 20 µm. Preferably, the pulse duration of the laser light applied in step B3) is between 1 ms to 20 ms, preferably 5 ms to 10 ms, most preferably 7 ms. Preferably, in step B3) the laser light is applied with a power output between 50 mW to 150 mW, with a focus diameter between 5 µm to 70 µm, and a pulse duration between 1 ms to 20 ms.

Method of Detecting Antibodies or Glycan-Binding Proteins (GBPs)

Saccharides and particularly glycans are an important class of vaccines and antibody binders and are particularly useful as markers in immunological assays for detection of antibodies or glycan-binding proteins, such as lectins, against pathogens containing in their capsule the respective saccharide or a fragment thereof.

Glycan-binding proteins, which are not glycan-specific antibodies, can be either lectins and sulfated glycosaminoglycan (GAG)-binding proteins.

Such assays comprise, for instance, glycan microarray or ELISA.

Thus an aspect of the present invention is directed to a method of detecting antibodies glycan-binding proteins in a test sample comprising contacting the test sample with a saccharide array obtained by an inventive method described herein and observing whether one or more saccharides or glycans are bound by an antibody in the test sample. The glycan microarrays obtained from the inventive methods described herein can be used in any common binding (competitive or non-competitive) assay known in the art (e.g. as described in *Chem Biol*, 2014, 38-50). Binding may be detected by direct fluorescence, wherein the antibody or glycan-binding protein is conjugated to a fluorophore or indirect fluorescence, wherein a secondary antibody directed against the primary antibody or glycan-binding protein is conjugated to a fluorophore, such as fluorescein isothiocyanate (FITC).

Thus, the present invention is also directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
 A) providing a solid support with at least one immobilized acceptor group for reacting with a saccharide;
 B) delivering the saccharide onto the solid support;
 C) applying a vapor of a solution of a glycosylation reagent in a solvent onto the solid support at a temperature below 20° C. in order to initiate a coupling reaction of the saccharide to the at least one immobilized acceptor group.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
 A) providing a solid support having a plurality of acceptor groups for reacting with a saccharide at discrete locations immobilized thereto;
 B) delivering at least one saccharide at the discrete locations on the surface of the solid support;
 C) applying a vapor of a solution of a glycosylation reagent in a solvent onto the solid support at a temperature below 20° C. in order to initiate a coupling reaction of the at least one saccharide to the plurality of acceptor groups immobilized at discrete locations to the solid support.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
 A) providing a solid support having a plurality of acceptor groups for reacting with a saccharide at discrete locations immobilized thereto;
 B) delivering at least one saccharide at the discrete locations on the surface of the solid support;
 C) applying a vapor of a solution of a glycosylation reagent in a solvent onto the solid support at a temperature below 20° C. in order to initiate a coupling reaction of the at least one saccharide to the plurality of acceptor groups immobilized at discrete locations to the solid support,
wherein the binding of the antibody to the one or more saccharides is observed by direct or indirect fluorescence.

In one embodiment, the present invention is directed to a method of detecting antibodies or glycan-binding proteins in a test sample comprising contacting the test sample with a saccharide array and observing whether one or more saccharides are bound by an antibody or saccharide-binding protein in the test sample, wherein the saccharide array is prepared by the following steps comprising
 A) providing a solid support having a plurality of acceptor groups for reacting with a saccharide at discrete locations immobilized thereto;
 B) delivering at least one saccharide at the discrete locations on the surface of the solid support;
 C') drying the solid support obtained in step B) under reduced pressure and/or heating;
 C) applying a vapor of a solution of a glycosylation reagent in a solvent onto the solid support at a temperature below 20° C. in order to initiate a coupling reaction of the at least one saccharide to the plurality of acceptor groups immobilized at discrete locations to the solid support.

In one embodiment, the present invention is directed to a method of detecting antibodies or glycan-binding proteins in a test sample comprising contacting the test sample with a saccharide array and observing whether one or more saccharides are bound by an antibody or saccharide-binding protein in the test sample, wherein the saccharide array is prepared by the following steps comprising
 A) providing a solid support having a plurality of acceptor groups for reacting with a saccharide at discrete locations immobilized thereto;
 B) applying at least one solution of a saccharide at the discrete locations on the surface of the solid support;
 C') drying the solid support obtained in step B) and evaporating the solvent of at the least one solution under reduced pressure and/or heating;

C) applying a vapor of a solution of a glycosylation reagent in a solvent onto the solid support at a temperature below 20° C. in order to initiate a coupling reaction of the at least one saccharide to the plurality of acceptor groups immobilized at discrete locations to the solid support.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
- A) providing a solid support having a plurality of acceptor groups for reacting with a saccharide at discrete locations immobilized thereto;
- B) delivering at least one saccharide at the discrete locations on the surface of the solid support;
- C') drying the solid support obtained in step B) under reduced pressure and/or heating;
- C) applying a vapor of a solution of a glycosylation reagent in a solvent onto the solid support at a temperature below 20° C. in order to initiate a coupling reaction of the at least one saccharide to the plurality of acceptor groups immobilized at discrete locations to the solid support;
- K) performing removal of protecting groups from the saccharide obtained in step C).

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
- A) providing a solid support having a plurality of acceptor groups for reacting with a saccharide at discrete locations immobilized thereto;
- B) delivering at least one saccharide at the discrete locations on the surface of the solid support;
- C) applying a vapor of a solution of a glycosylation reagent in a solvent onto the solid support at a temperature below 5° C., more preferably below 0° C., more preferably between −78° C. and 0° C. and most preferably between −20° C. and 0° C. in order to initiate a coupling reaction of the at least one saccharide to the plurality of acceptor groups immobilized at discrete locations to the solid support.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
- A) providing a solid support having a plurality of acceptor groups for reacting with a saccharide at discrete locations immobilized thereto;
- B) delivering at least one saccharide at the discrete locations on the surface of the solid support;
- C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support, wherein the ratio of the solvent and the glycosylation reagent in the vapor is in the range of 1:10 to 100,000:1.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
- A) providing a solid support having a plurality of acceptor groups for reacting with a saccharide at discrete locations immobilized thereto;
- B) delivering at least one saccharide at the discrete locations on the surface of the solid support;
- C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support, wherein the solvent is an aprotic organic solvent selected from: methylene chloride, acetonitrile, chloroform, diethyl ether, 1,4-dioxane, methyl tert-butyl ether, toluene and ethyl acetate.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
- A) providing a solid support having a plurality of acceptor groups for reacting with a saccharide at discrete locations immobilized thereto;
- B) delivering at least one saccharide at the discrete locations on the surface of the solid support;
- C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support, wherein the glycosylation reagent is a Lewis acid selected from: AgOTf, $BF_3 \cdot OEt_2$, trimethylsilyl trifluoromethanesulfonate (TMSOTf), trifluoromethanesulfonic acid (TfOH), trifluoromethanesulfonic anhydride ($Tf_2O$, triflic anhydride), lanthanoid(III) triflates, NIS/AgOTf, NIS/TfOH or dimethyl(methylthio)sulfonium trifluoromethanesulfonate (DMTST), preferably trimethylsilyl trifluoromethanesulfonate (TMSOTf), trifluoromethanesulfonic acid (TfOH), trifluoromethanesulfonic anhydride, or NIS/TfOH.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
- A) providing a solid support having a plurality of acceptor groups for reacting with a saccharide at discrete locations immobilized thereto;
- B) delivering at least one saccharide at the discrete locations on the surface of the solid support;
- C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support, wherein the at least one saccharide is a protected glycosyl donor comprising a glycal, epoxide or orthoester group or having a leaving group at the reducing end selected from halogen, $-O-C(=NH)-CCl_3$, $-O-C(=NPh)-CF_3$, $-OAc$, $-SR^5$, $-SO-Ph$, $-SO_2-Ph$, $-O-(CH_2)_3-CH=CH_2$, $-O-P(OR^5)_2$, $-O-PO(OR^5)_2$, $-O-CO-OR^5$, $-O-CO-SR^5$, $-O-CS-SR^5$, $-O-CS-OR^5$,

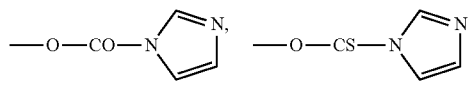

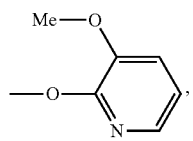

or wherein $R^5$ represents an alkyl or aryl group.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
- A) providing a solid support having a plurality of acceptor groups for reacting with a saccharide at discrete locations immobilized thereto;
- B) delivering at least one monosaccharide at the discrete locations on the surface of the solid support;
- C) applying a vapor of a solution of a glycosylation reagent in a solvent onto the solid support at a temperature below 20° C., in order to initiate a coupling reaction of the at least one monosaccharide to the plurality of acceptor groups immobilized at discrete locations to the solid support, wherein the at least one monosaccharide is a protected glycosyl donor having a leaving group at its reducing end selected from halogen, $-O-C(=NH)-CCl_3$, $-O-C(=NPh)-CF_3$, $-O-(CH_2)_3-CH=CH_2$, $-O-PO(OR^5)_2$, or $-SR^5$, wherein $R^5$ represents $-CH_3$, $-CH_2CH_3$, $-CH_2CH_2CH_3$, $-(CH_2)_3CH_3$, or -Tol.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
- A) providing a solid support having a plurality of acceptor groups for reacting with a saccharide at discrete locations immobilized thereto;
- B) delivering at least one saccharide at the discrete locations on the surface of the solid support;
- C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support, wherein in step B) the at least one saccharide is delivered as a solid, from a solution or in a polymer matrix onto the solid support.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
- A) providing a solid support having a plurality of acceptor groups for reacting with a saccharide at discrete locations immobilized thereto;
- B) delivering a solution of at least one saccharide at the discrete locations on the surface of the solid support;
- C') drying the solid support obtained in step B) under reduced pressure and/or heating;
- C) applying a vapor of a solution of a glycosylation reagent in a solvent onto the solid support at a temperature below 20° C., in order to initiate a coupling reaction of the at least one saccharide to the plurality of acceptor groups immobilized at discrete locations to the solid support.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is prepared by the following steps comprising
- A) providing a solid support having a plurality of acceptor groups for reacting with a saccharide at discrete spots covalently attached thereto;
- B) delivering a solution of at least one saccharide at the discrete spots on the surface of the solid support;
- C') drying the solid support obtained in step B) under reduced pressure and/or heating;
- C) applying a vapor of a solution of a glycosylation reagent in a solvent onto the solid support at a temperature below 5° C., in order to initiate a coupling reaction of the at least one saccharide to the plurality of acceptor groups covalently attached at discrete spots to the solid support,
- K) performing removal of protecting groups from the saccharide obtained in step C), wherein the solid support is a cellulose membrane and wherein the at least one saccharide is a protected glycosyl donor having a leaving group at its reducing end selected from halogen, $-O-C(=NH)-CCl_3$, $-O-C(=NPh)-CF_3$, $-O-(CH_2)_3-CH=CH_2$, $-O-PO(OR^5)_2$, or $-SR^5$, wherein $R^5$ represents $-CH_3$, $-CH_2CH_3$, $-CH_2CH_2CH_3$, $-(CH_2)_3CH_3$, or -Tol.

In one embodiment, the present invention is directed to a method of detecting antibodies or glycan-binding proteins in a test sample comprising contacting the test sample with a saccharide array and observing whether one or more saccharides are bound by an antibody or glycan-binding protein in the test sample, wherein the saccharide array is a high-density saccharide array prepared by the following steps comprising
- A3) providing a solid support with acceptor groups immobilized at discrete spots, and A3') providing a donor support comprising a film layer, in which at least one saccharide is present, and an intermediate layer between the support and the film layer, B3) selectively transferring of material of the at least one saccharide from the donor support to the solid support of step A3) and site-specific fixing of the transferred material to the discrete spots of the solid support by electromagnetic irradiation comprising laser light;

C3) applying a vapor of a solution of a glycosylation reagent in a solvent onto the solid support at a temperature below 20° C. in order to initiate a coupling reaction of the at least one saccharide to the acceptor groups immobilized at discrete locations to the solid support, wherein the selective transfer and the site-specific fixing of the at least one saccharide molecule from the donor support to the solid support is without direct contact between the supports and the at least one saccharide molecule is transferred in liquid or gaseous form, and wherein the intermediate layer comprises polyimide, polycaprolactone, polystyrene or polyethylene.

Saccharide Synthesizer

A further aspect of the present invention is directed to a saccharide synthesizer comprising:
- a substrate, the substrate having a surface and being configured to support a solid support with at least one immobilized acceptor group for reacting with a saccharide;
- means for delivering a saccharide to a solid support with at least one immobilized acceptor group for reacting with a saccharide supported by the substrate;
- a chamber comprising
  - a process space;
  - a vapor supply in fluid communication with the process space, the vapor supply configured to supply a vapor comprising a solvent and a glycosylation reagent to the process space;
  - a cooling element positioned within the processing chamber configured to cool the solid support by heat transfer through the substrate;
  - an exhaust port in the processing chamber configured in fluid communication with an isolation valve;
  - a purge gas supply in fluid communication with the process space, the purge gas supply configured to supply a purge gas to the process space effective to displace the vapor from the process space, wherein the substrate is positioned in the process space of the chamber.

In a preferred embodiment the means for delivering a saccharide to a solid support comprises a capillary needle which is in fluid connection with a reservoir containing a saccharide, optionally a syringe connected to said capillary needle, or optionally a microactuator connected to said capillary needle; or a laser for transferring the saccharide in a polymer matrix onto the solid support. Thus, the present invention is directed to a saccharide synthesizer comprising:
- a substrate, the substrate having a surface and being configured to support a solid support with at least one immobilized acceptor group for reacting with a saccharide;
- means for delivering a saccharide to a solid support with at least one immobilized acceptor group for reacting with a saccharide supported by the substrate;
- a chamber comprising
  - a process space;
  - a vapor supply in fluid communication with the process space, the vapor supply configured to supply a vapor comprising a solvent and a glycosylation reagent to the process space;
  - a cooling element positioned within the processing chamber configured to cool the solid support by heat transfer through the substrate;
  - an exhaust port in the processing chamber configured in fluid communication with an isolation valve;
  - a purge gas supply in fluid communication with the process space, the purge gas supply configured to supply a purge gas to the process space effective to displace the vapor from the process space, wherein the substrate is positioned in the process space of the chamber, and wherein the means for delivering a saccharide to a solid support comprises a capillary needle which is in fluid connection with a reservoir containing a saccharide, optionally a syringe connected to said capillary needle, or optionally a microactuator connected to said capillary needle; or a laser for transferring the saccharide in a polymer matrix onto the solid support.

In a preferred embodiment the cooling element of the chamber is capable of cooling the solid support below a temperature of 5° C. Thus, the present invention is directed to a saccharide synthesizer comprising:
- a substrate, the substrate having a surface and being configured to support a solid support with at least one immobilized acceptor group for reacting with a saccharide;
- means for delivering a saccharide to a solid support with at least one immobilized acceptor group for reacting with a saccharide supported by the substrate;
- a chamber comprising
  - a process space;
  - a vapor supply in fluid communication with the process space, the vapor supply configured to supply a vapor comprising a solvent and a glycosylation reagent to the process space;
  - a cooling element positioned within the processing chamber configured to cool the solid support by heat transfer through the substrate;
  - an exhaust port in the processing chamber configured in fluid communication with an isolation valve;
  - a purge gas supply in fluid communication with the process space, the purge gas supply configured to supply a purge gas to the process space effective to displace the vapor from the process space, wherein the substrate is positioned in the process space of the chamber, and wherein the cooling element of the chamber cools the solid support below a temperature of 5° C.

FIGS. 6A, B and C show some configurations of the chamber of the inventive synthesizer. The chamber comprises at least one inlet for vapor supply or purge gas supply and one outlet (exhaust port) for displacing the vapor or applying a vacuum.

Preferably, the vapor supply and the purge gas supply are in fluid communication with the process space via a valve. Preferably, the vapor supply is arranged on a side wall of the chamber. Preferably, the vapor supply is configured to apply a laminar flow of the vapor onto the solid support.

In a preferred embodiment the at least one inlet for vapor supply and the one outlet (exhaust port) for displacing the vapor or applying a vacuum are arranged on top of the chamber. Preferably the e at least one inlet for vapor supply and the one outlet (exhaust port) for displacing the vapor or applying a vacuum are located at opposite positions of the top of the chamber in order to allow a laminar flow of the vapor onto the solid support.

In a preferred embodiment, the saccharide synthesizer comprises:
- a substrate, the substrate having a surface and being configured to support a solid support with at least one immobilized acceptor group for reacting with a saccharide;
- means for delivering a saccharide to a solid support with at least one immobilized acceptor group for reacting with a saccharide supported by the substrate;
- a chamber comprising
  - a process space;
  - a vapor supply in fluid communication with the process space, the vapor supply configured to supply a vapor comprising a solvent and a glycosylation reagent in laminar flow to the process space;
  - a cooling element positioned within the processing chamber configured to cool the solid support by heat transfer through the substrate;
  - an exhaust port in the processing chamber configured in fluid communication with an isolation valve;
  - a purge gas supply in fluid communication with the process space, the purge gas supply configured to supply a purge gas to the process space effective to displace the vapor from the process space,
wherein the substrate is positioned in the process space of the chamber and wherein the vapor supply and the purge gas supply are in fluid communication with the process space via a valve.

A further aspect of the present invention is directed to a system for producing saccharides comprising
1) a saccharide synthesizer comprising:
   - a substrate, the substrate having a surface and being configured to support a solid support with at least one immobilized acceptor group for reacting with a saccharide;
   - means for delivering a saccharide to a solid support with at least one immobilized acceptor group for reacting with a saccharide supported by the substrate;
   - a chamber comprising
     - a process space;
     - a vapor supply in fluid communication with the process space, the vapor supply configured to supply a vapor comprising a solvent and a glycosylation reagent to the process space;
     - a cooling element positioned within the processing chamber configured to cool the solid support by heat transfer through the substrate;
     - an exhaust port in the processing chamber configured in fluid communication with an isolation valve;
     - a purge gas supply in fluid communication with the process space, the purge gas supply configured to supply a purge gas to the process space effective to displace the vapor from the process space,
   wherein the substrate is positioned in the process space of the chamber; and
2) a solid support with at least one immobilized acceptor group for reacting with a saccharide.

DESCRIPTION OF THE FIGURES

FIG. 4 provides examples of interconnecting molecules for immobilizing saccharides to solid support.

Figure 1:
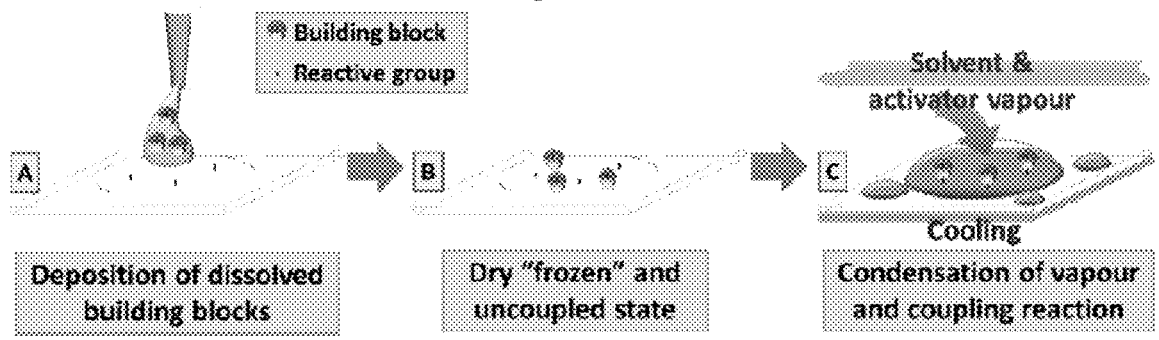
FIG. 1 illustrates the inventive method for producing a saccharide on a cellulose membrane by spotting a solution of saccharide building block on to the cellulose membrane.
Figure 2:
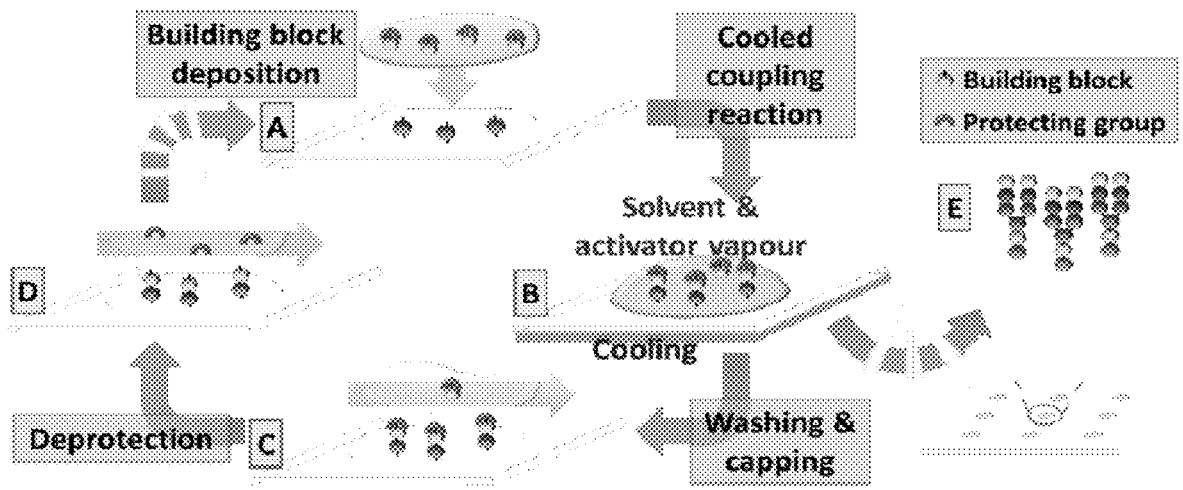
FIG. 2 illustrates the inventive method for high-throughput synthesis of a high-density saccharide array.
Figure 3:
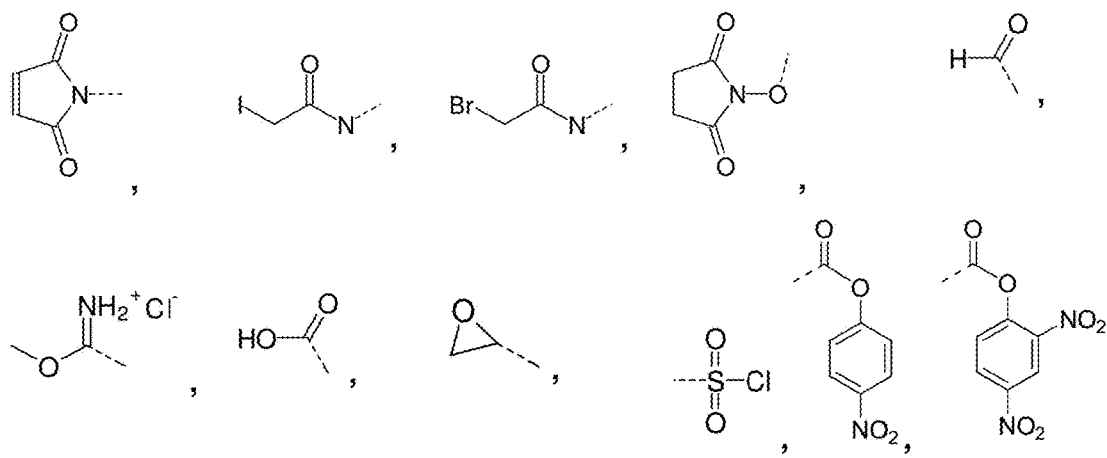
FIG. 3 provides examples of commercially available anchoring groups.

The following examples are included to demonstrate preferred embodiments of the invention. It should be appreciated by those skilled in the art that the techniques disclosed in the examples, which follow represent techniques discovered by the inventor to function well in the practice of the invention, and thus can be considered to constitute preferred modes for its practice. However, those skilled in the art should, in light of the present disclosure, appreciate that many changes can be made in the specific embodiments, which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Chemicals & Reagents

Unless otherwise stated, all chemicals and reagents were acquired from Sigma-Aldrich, TCI, Iris Biotech, ROTH, Acros, Merck, or Alfa Aesar and were of the highest purity available. Solid supports were obtained from PolyAn, Schott, or SurModics. Saccharide building blocks were obtained from GlycoUniverse or prepared by using a commercial saccharide synthesizer.

Example 1: Optimization of Vapor Triggered Glycosylation on a Functionalized Glass Slide 1.1 Acceptor slide preparation: Commercially available amine-functionalized glass slides from PolyAn GmbH were used as acceptor slides. The slides were functionalized with a $C_{11}$-spacer (see FIG. 7) in presence of diisopropyl-carbodiimide (DIC) and hydroxybenzotriazole (HOBt) by contacting two slides with the Fmoc-protected $C_{11}$-spacer 4 in between (sandwich) overnight. Unreacted free amine groups on the slide surface were capped using a mixture of $Ac_2O$/DIPEA/DMF. Fmoc-group of the $C_{11}$-spacer was removed by treating the slide with 20% piperidine in DMF. Galactose acceptor molecule 6 was coupled to the C11-acceptor in presence of DIC and HOBt by contacting two slides with the acceptor 6 in between (sandwich) overnight. Unreacted amino groups were capped using a mixture of $Ac_2O$/DIPEA/DMF. The Fmoc group was removed treating the slide with 20% piperidine in DMF.

1.2 Donor slide preparation: All donor slides were generated by spin-coating a solution of the glycosyl donor 8 (building block) and an inert polymer matrix (SLEC PLT 7552, Sekisui Chemical GmbH, Düsseldorf/Germany) in dichloromethane on a glass slide covered with a polyimide foil (Kapton®). The inert polymer matrix forms a protective layer and shields the building block from environmental influences, while the Kapton® foil is needed for laser light absorption and heat induction. The donor composition is shown in table 1 below.

TABLE 1

Composition of donor solution.

| entry | glycosyl donor 8 (mg) | Matrix-SLEC (mg) | dichloromethane (mL) |
|---|---|---|---|
| 1 | 50 | 50 | 1 |
| 2 | 25 | 25 | 0.5 |

Figure 10:
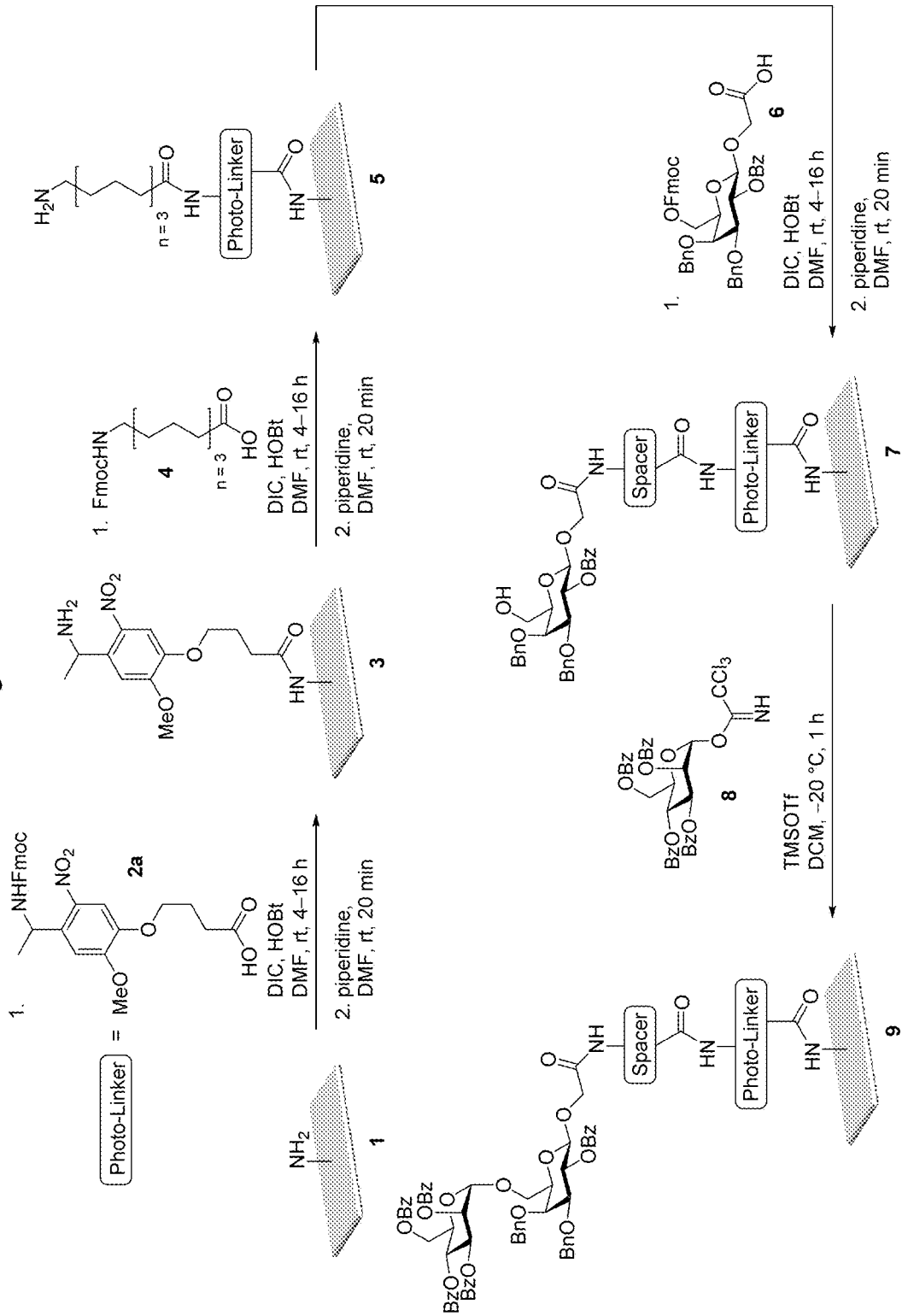
FIG. 10 shows complete disaccharide synthesis on glass slide using the inventive method.
Figure 10:
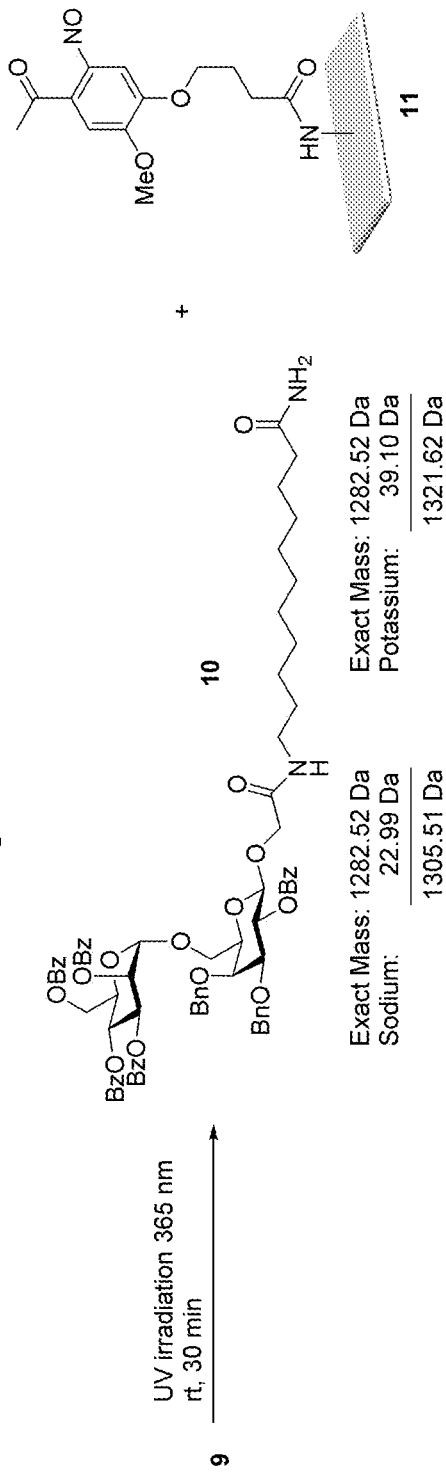

Chemical structures of compounds 4, 6 and 8 are shown FIG. 10.

1.3 Laser transfer: The glycosyl imidate 8 was transferred with laser induced forward transfer (cLIFT) onto the acceptor slide using the following laser parameters:

100 mW, 20 μm focus diameter, 7 ms pulse duration, 200 μm spot pitch. The donor slide was placed on top of the acceptor, and the laser light reached the Kapton® foil. The heat, which is produced via laser irradiation, deforms the donor slide, thus bringing the two layers in contact. The Kapton® foil, which is stable under short-term heat exposure, expands slightly due to the heat from the laser, transferring the desired compound from the donor to the acceptor slide.

Figure 8:
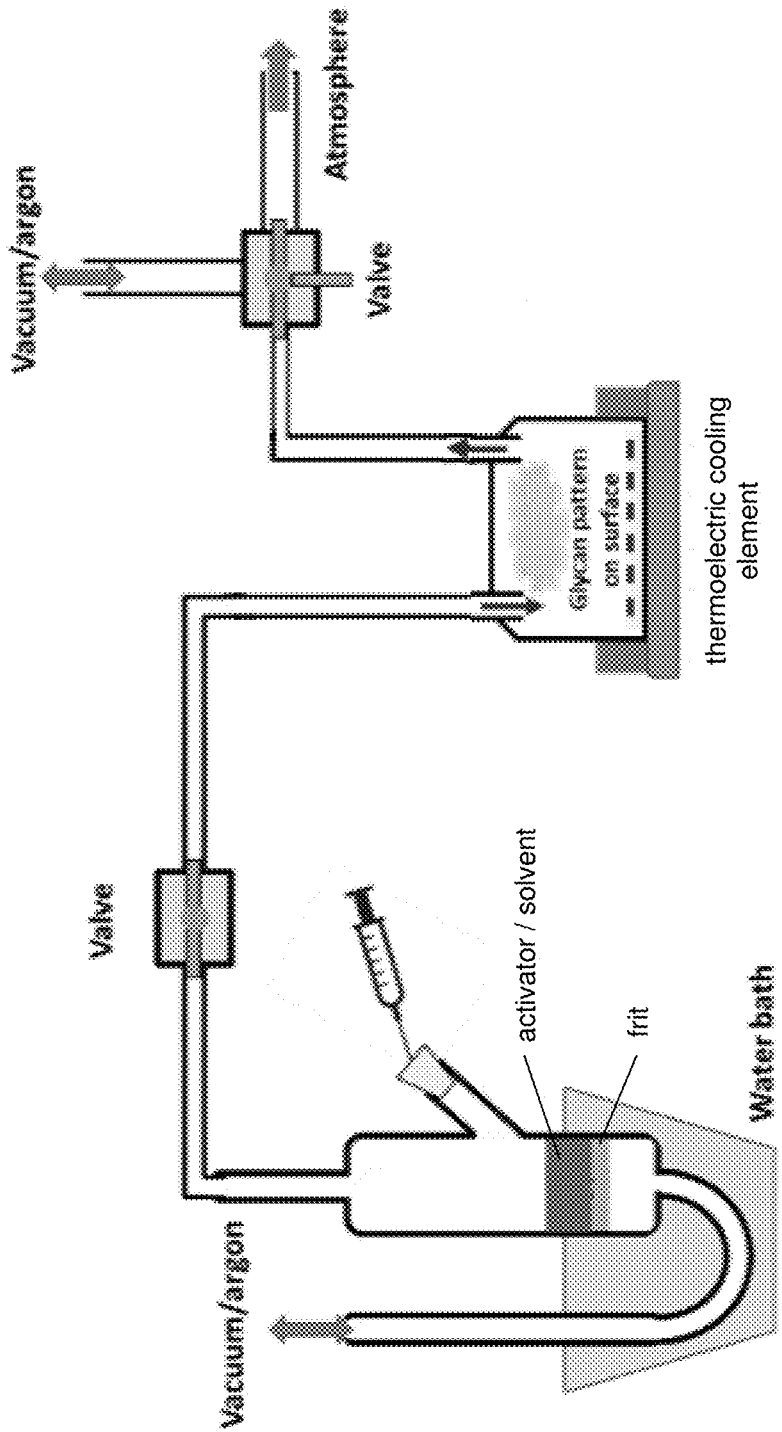
FIG. 8 shows a setup of a vapor annealing coupling chamber and a vapor generator; the U-shaped vapor generator comprises a frit, a gas inlet, a gas outlet, an inlet for glycosylation reagent located above the frit, the generator is located in a water bath of 50° C.; the coupling chamber is equipped with a thermoelectric cooling element for controlling the reaction temperature, wherein the temperature can be controlled with a computer.

1.4 Vapor coupling (CVAS): The acceptor slide covered with building block and matrix material was placed on a thermoelectric cooling element in a chamber for glycosylation as shown in FIG. 8. The chamber was then evacuated through the connection (connected to a common vacuum gas manifold, i.e. Schlenk line) on top of the chamber and flushed with argon for three times. Then, the temperature was reduced to −12° C. under inert atmosphere to achieve satisfactory deposition of solvent and activator inside the setup at low temperature. The chilled surface area of the chamber is 56.3 $cm^2$ (7.5 cm×7.5 cm), where the slide is placed, while for the whole vapor chamber volume is 338 $cm^3$ (13 cm×13 cm×2 cm).

Figure 9:
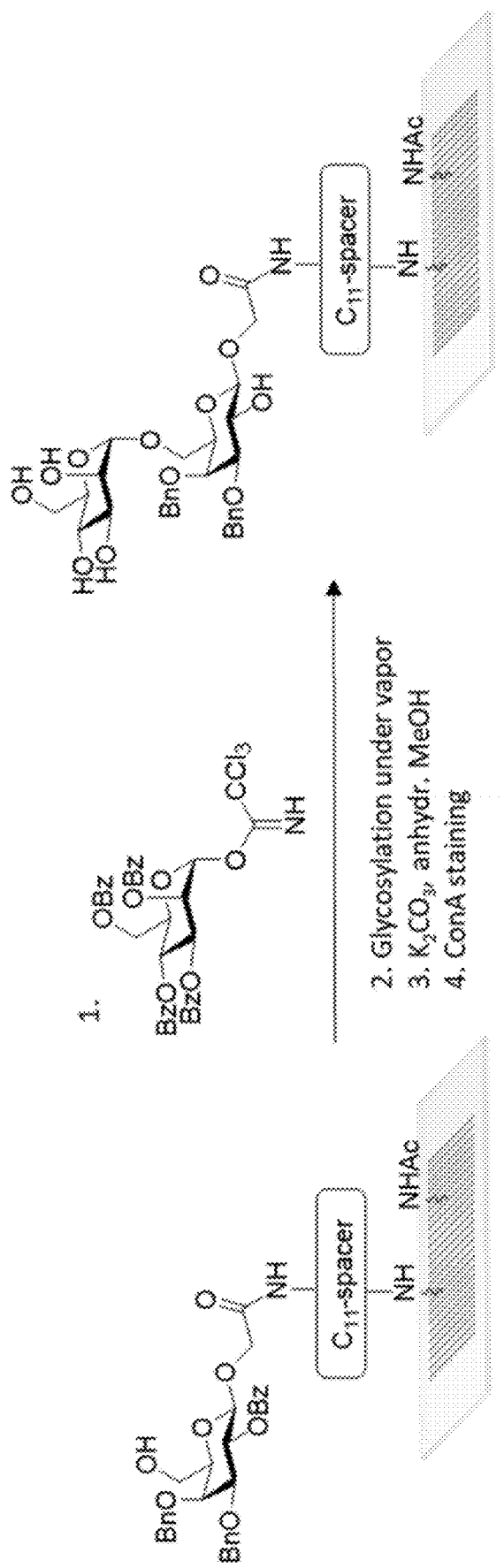
FIG. 9 shows the reaction scheme of a vapor-triggered glycosylation on a slide.

The glycosylation solution containing dichloromethane and activator was bubbled for 2.3 min under inert atmosphere (FIG. 8) until complete transfer of the solution inside the glycosylation-vapor chamber. The conditions for the glycosylation reaction are summarized in Table 2. The acceptor slide is left to react under vapor for 30 min in a closed setup. After completion, the acceptor-setup was warmed up to rt under vacuum. Then, the slide was removed from the setup and washed with dimethylformamide and dichloromethane. Deprotection of the benzoyl groups was accomplished under inert atmosphere using anhyd. methanol and $K_2CO_3$ overnight. Screening of the result was achieved after fluorescent staining with the tetravalent fluorescently red labelled (λ=633 nm) Concanavalin A lectin (binds selectively to α-mannopyranosyl residues), to verify the successful glycosylation (see FIG. 9).

TABLE 2

Conditions of glycosylation reaction.

Figure 7:
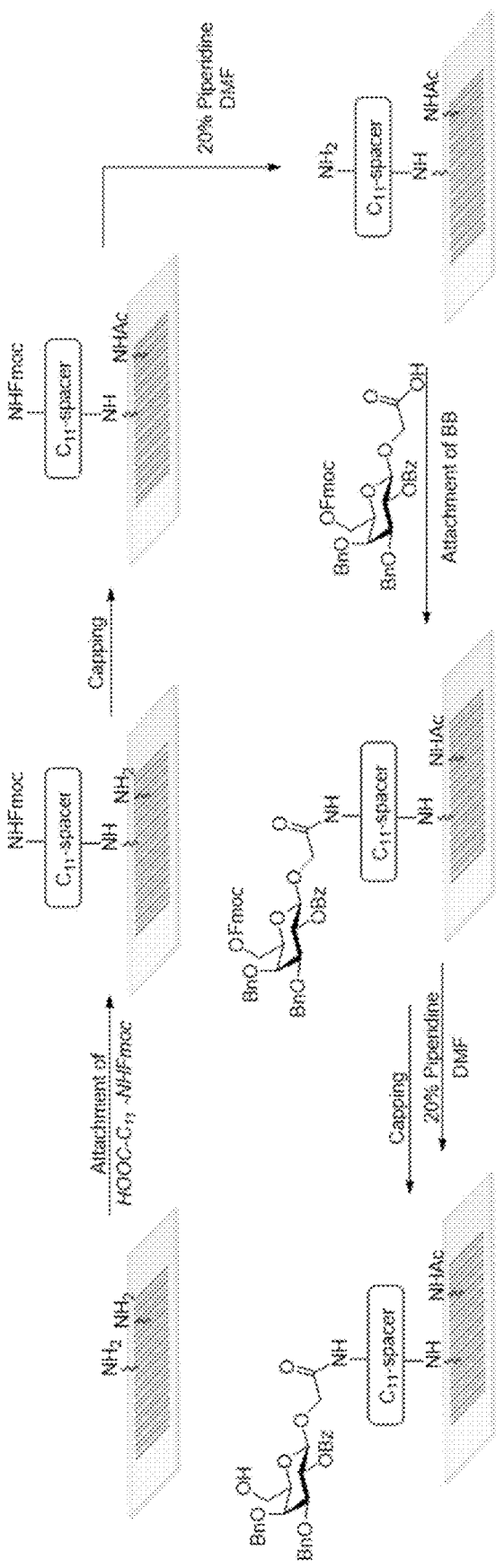
FIG. 7 shows the preparation of acceptor slide for laser transfer of a glycosyl donor.

Glycosylation conditions using setup shown in FIG. 7

| Entry | Donor Preparation | Bubbling time (min) | Dichloromethane (μL) | TMSOTf (μL) | $T_{glyc}$ (° C.) | $T_{bath}$ (° C.) | Reaction time |
|---|---|---|---|---|---|---|---|
| A | Entry 1 | 2.3 | 1500 | 150 μL | −12 | 55 | 30 min |
| B | Entry 2 | 1.0 | 400 | 25 μL | −12 | 57 | 30 min |
| C | Entry 2 | 1.3 | 400 | 75 μL | −12 | 40 | 30 min |
| D | Entry 1 | 1.3 | 400 | 75 μL | −12 | 40 | 30 min |

In all four runs spots were observed after Concanavalin A staining, indicating the successful glycosylation of immobilized acceptor 6 with donor 8. Most prominent and homogenous spots were observed in runs at lower temperature of the glycosylation mixture, C and D; thereby leading to the conclusion that a slow and homogeneous transfer of the solution inside the setup takes place.

Figure 5:
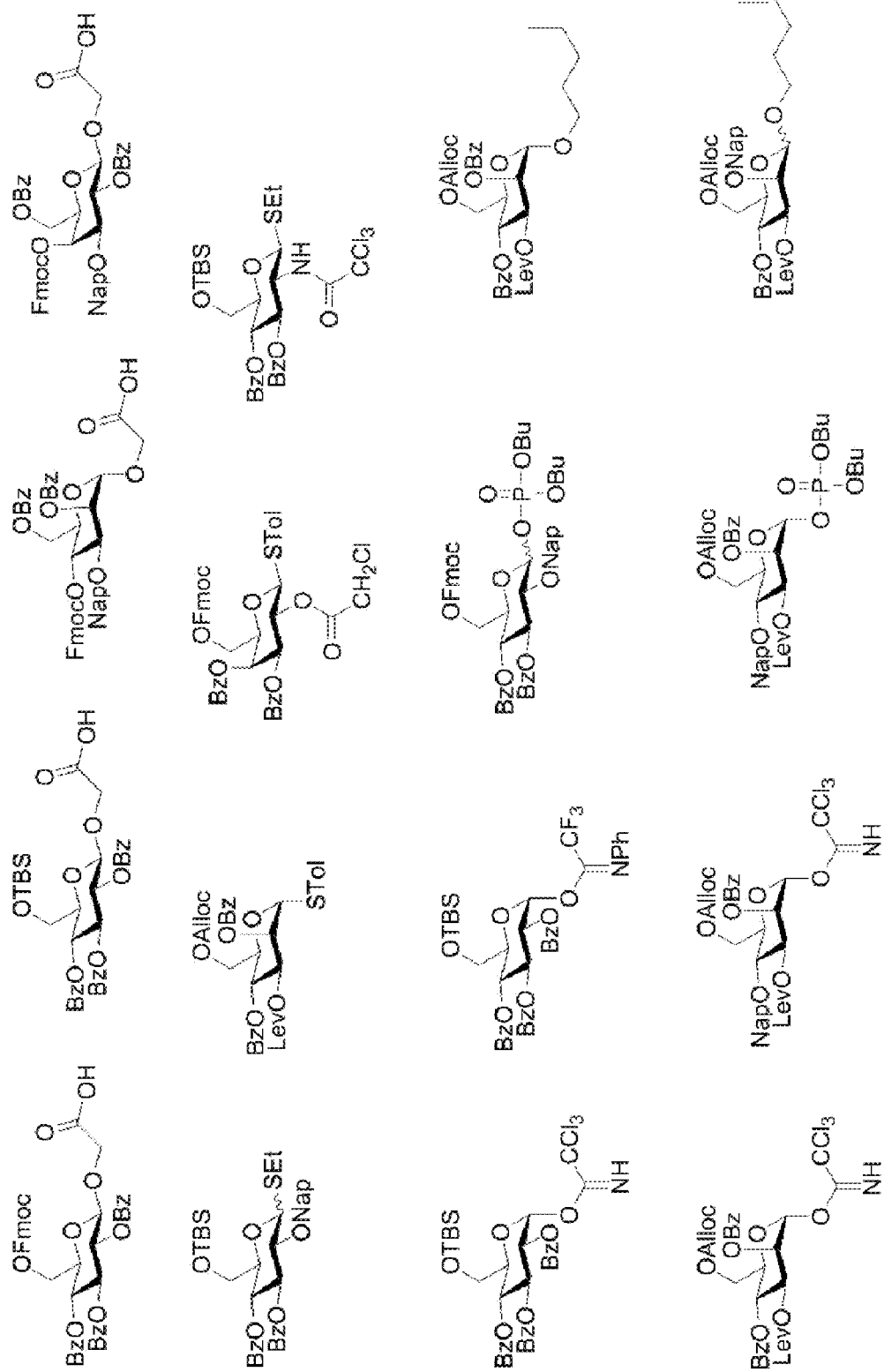
FIG. 5 shows the structures of exemplarily saccharide building blocks which can be used in the present invention.
Figure 6A:
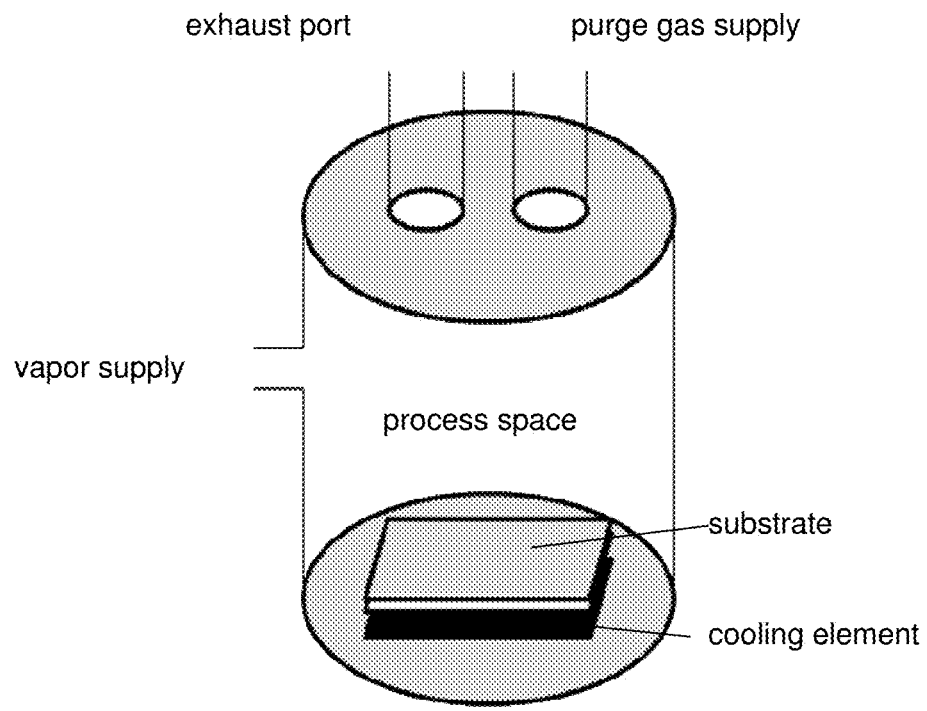
FIGS. 6A, B and C illustrate different embodiments of the chamber of the inventive synthesizer.
Figure 6B:
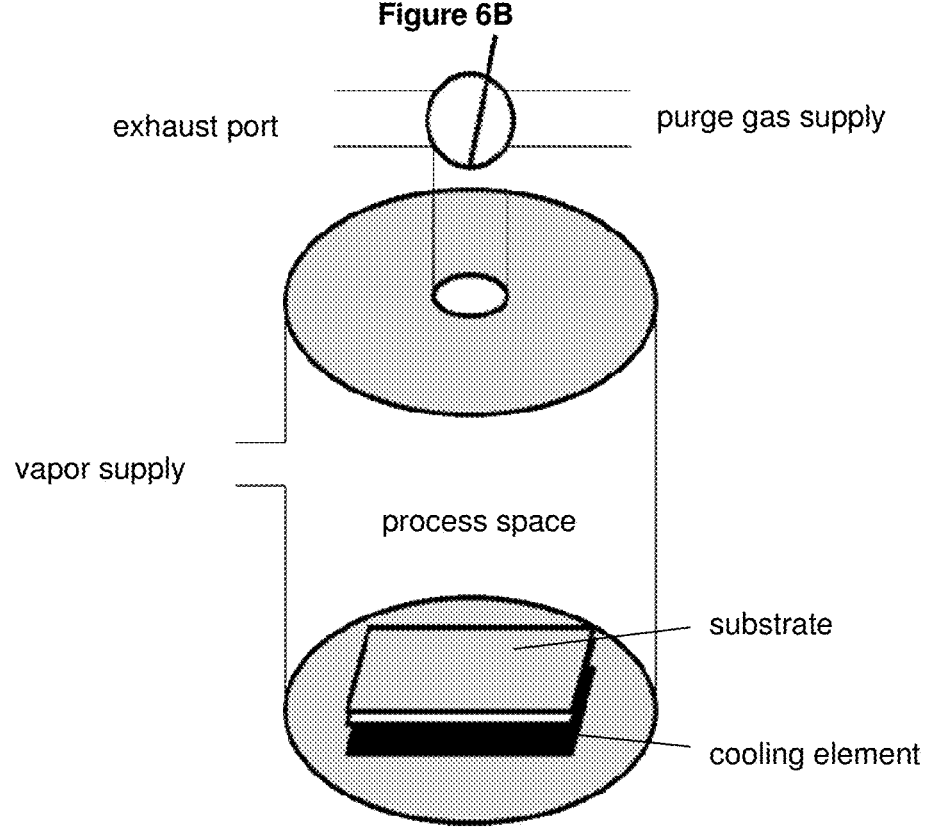
Figure 6C:
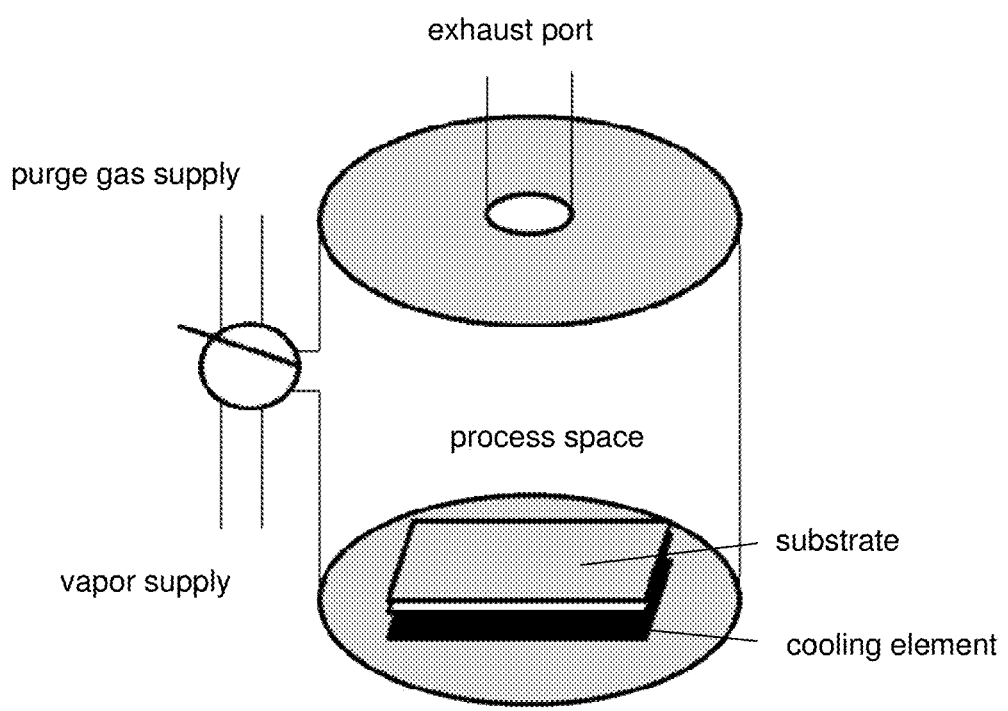

Example 2: Vapor Triggered Glycosylation on a Functionalized Glass Slide 2.1 Acceptor slide preparation: The vapor triggered glycosylation reaction of a glycosyl donor and a glycosyl acceptor on a functionalized glass slide (solid support) was accomplished on a commercially available 3D amine microarray slide from PolyAn GmbH (Berlin). In this case also other functionalized glass slides from other companies like carboxyl-(NHS-activated or not), epoxy-, maleimide-, thiol-, azide-, hydroxyl-, tetrazine-, aldehyde- or alkyne-surfaces may be used. Therefore the functional groups can be used on the surfaces directly for the attachment of a linker, spacer, interconnecting molecule (see FIG. 4) or saccharide building block (see FIG. 5) or convert them into another functional group, which can then be used for connection between the above mentioned species and the glass slide. Another option would be a self-synthesized microarray glass slide for this approach.

To perform the glycosylation method—the glycosylation on a solid support using vapor—the 3D amine microarray slide from PolyAn GmbH (Berlin) was functionalized for this purpose. Therefore, first the commercially available (Iris Biotech GmbH, Marktredwitz) photocleavable linker 2a were attached on the slide, followed by spacer 4 and finally by modified galactose building block 6 (FIG. 10). All these attachments were done in solution by standard amide bond formation using the conditions shown below.

Conditions for Photo-Linker 2a Attachment:
  Photo-linker 2a: 26.0 mg, 50 µmol
  DIC: 23.2 µl, 18.9 mg, 150 µmol
  HOBt: 6.76 mg, 50 µmol
  DMF: 250 µL
  Temperature: rt
  Time: 4-16 h Conditions for Spacer 4 Attachment:
  Spacer 4: 21.2 mg, 50 µmol
  DIC: 23.2 µl, 18.9 mg, 150 µmol
  HOBt: 6.76 mg, 50 µmol
  DMF: 250 µL
  Temperature: rt
  Time: 4-16 h Conditions for Galactose Building Block 6 Attachment:
  Galactose 6: 18.6 mg, 25 µmol
  DIC: 11.6 µl, 9.45 mg, 75 µmol
  HOBt: 3.40 mg, 25 µmol
  DMF: 250 µL
  Temperature: rt
  Time: 4-16 h The galactose building block was functionalized with a free carboxylic acid group to form an amide bond between the sugar moiety and the solid support. With the prefunctionalized surface 7 (FIG. 10) in hand, the vapor induced glycosylation method on a solid support was realized.

2.2 Donor slide preparation: First of all, the donor slide was prepared as followed for the laser induced forward transfer (cLIFT) of the glycosyl donor 8 (structure shown in FIG. 10).

Conditions for Spin Coating Process of Glycosyl Imidate 8:
  Glycosyl imidate 8: 50 mg
  Polymer matrix (S-Lec): 50 mg
  DCM (dry): 1.00 mL
  Spin coater speed: 80 rounds per second
  Temperature: rt 2.3 Laser transfer: The glycosyl imidate 8 was transferred with laser induced forward transfer (cLIFT) onto the acceptor slide 7 using the following laser parameters: 100 mW, 20 µm focus diameter, 7 ms pulse duration, 200 µm spot pitch. For the detection of the molecules via mass spectrometry the whole surface area of the donor slide was transferred to the acceptor slide and for the detection of the molecules using fluorescently labeled Concanavalin A lectin (binds selectively to α-mannopyranosyl residues) a spot pattern was transferred to the acceptor slide (in this case no linker or spacer is needed). Thereby no coupling reaction is initiated, which is very important for the process. The amount of the building block which is transferred with this approach is typically in a micro to nanomolar range. Approach is typically in a micro to nanomolar range.

Figure 13:
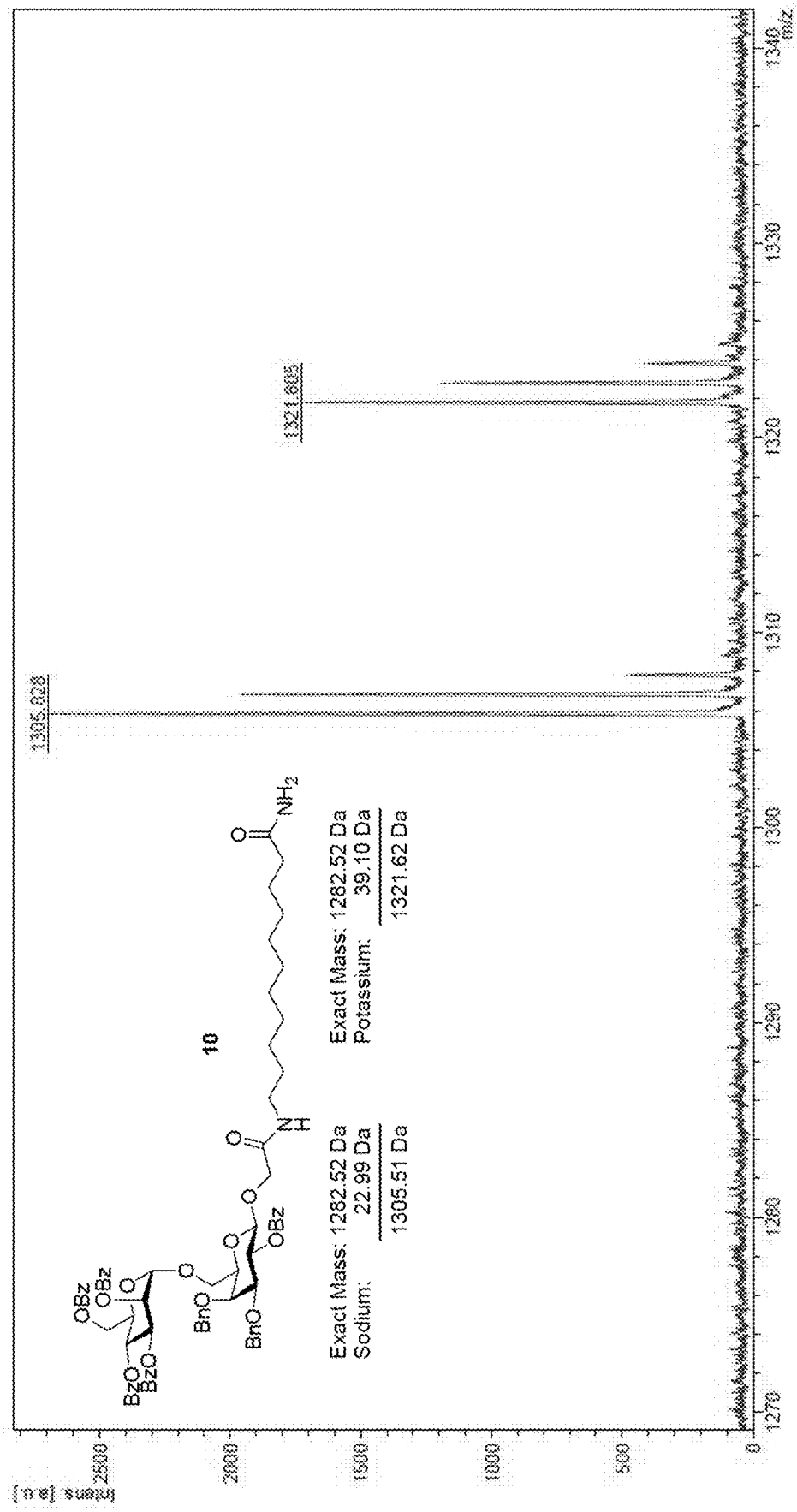
FIG. 13 shows MALDI-TOF-MS spectra of compound 10.

2.4 Vapor coupling (CVAS): The acceptor slide covered with building block and matrix material was placed in the chamber shown in FIG. 11 on a steel block. The chamber was then evacuated through the connection (connected to a common vacuum gas manifold, i.e. Schlenk line) on top of the chamber and flushed with argon for three times. The valve to the Schlenk line was closed and the whole setup was placed in the freezer at −20° C. for 1.5 h chilling the steel surface. The chamber was taken out of the freezer and was reconnected to the Schlenk line and evacuated and flushed with argon once more (the valve to the Schlenk line was kept open). Through the neck on the side of the chamber 20 mL of dry dichloromethane (DCM) were added into the chamber around the cold metal block. Additionally 400 µL of TMSOTf were added the same way. The chamber was evacuated for just as short as possible, switching the Schlenk line valve on and off by hand and then a constant flow of argon was connected to the chamber and the glycosylation was carried out for 1 h while the temperature inside the chamber increases slowly up to room temperature. To quench the reaction 1.00 mL of triethylamine were poured on the slide through the neck on the side of the chamber. The slide was taken out of the chamber, washed with different solvents and the molecule 10 was cleaved from the glass substrate via UV irradiation for the mass spectrometry approach and detected by MALDI-TOF-MS (FIG. 13). For the lectin staining approach after deprotection of the benzoyl groups ($K_2CO_3$ in MeOH) on the sugar moiety, the result was visualized by incubation of the slide with fluorescently labeled Concanavalin A in a HEPES-buffer and subsequent fluorescence scan.

Example 3: Glycosylation on Functionalized Membranes

Cellulose membranes functionalized with β-alanine (A, see 12A in scheme below) were obtained from AIMS Scientific Products GmbH and polypropylene membranes (B, see 12B in scheme below) were obtained from AIMS Scientific Products GmbH (hydroxy-functionalized) and PolyAn GmbH (amino-functionalized). The membranes were functionalized with a photo cleavable linker 2a, a spacer 4 and the glycosyl imidate 6 to obtain modified cellulose and polypropylene membrane. An exemplarily modified cellulose membrane 12A is shown below:

Membrane: Cellulose or Polypropylene

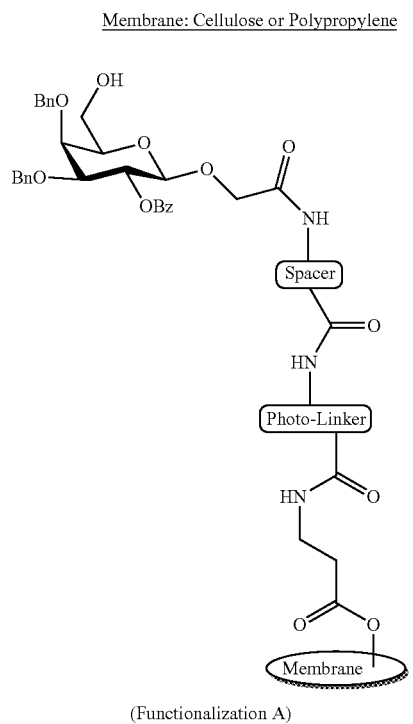

(Functionalization A)

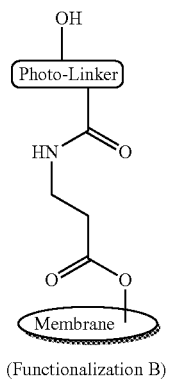

(Functionalization B)

Four different glycosylation reactions were tested on functionalized membranes A and B using galactose, mannose and glucose donors 8, 13, 14, and 15. The setup used for the vapor triggered glycosylation reactions is represented in FIG. 8.

TABLE 3

Conditions and results of glycosylation reactions on membranes.

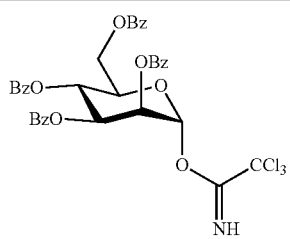

8

| Membrane material & functionalization | Spotting conditions | Solvent (μL) | Activator TMSOTf (μL) | Temperature (°C) | Bubbling time (min) | Reaction time (min)/Result |
|---|---|---|---|---|---|---|
| Membrane Cellulose A | inert | 1000 DCM | 70 | −12° C. to rt | 2 | 30/FC |
| | inert | 1000 DCM | 70 | −12° C. to rt | 1.5 | 30/SM |
| | ambient | 1000 DCM | 70 | −12° C. to rt | 2 | 30/NC |
| | inert | 1000 Tol | 70 | −12° C. to rt | 4.5 | 30/SM |
| | inert | 1000 Tol | 100 | −12° C. to rt | 4.5 | 30/SM |
| | inert | 900 DCM + 100 Tol | 70 | −12° C. to rt | 2 | 30/SM |

TABLE 3-continued

Conditions and results of glycosylation reactions on membranes.

| Membrane material & functionalization | Spotting conditions | Solvent (μL) | Activator TMSOTf (μL) | Temperature (° C.) | Bubbling time (min) | Reaction time (min) Result |
|---|---|---|---|---|---|---|
| Membrane Cellulose B | inert | 1000 DCM | 75 | −12° C. to rt | 2 | 30/FC |

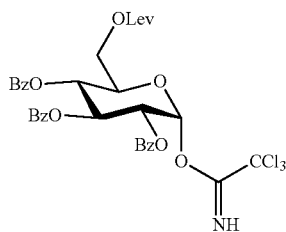

13

| Membrane Cellulose A | inert<br>inert | 1000 DCM<br>1000 DCM | 70<br>70 | −12° C. to rt<br>−12° C. to rt | 1<br>1.5 | 30/SM, P<br>30/SM, P |

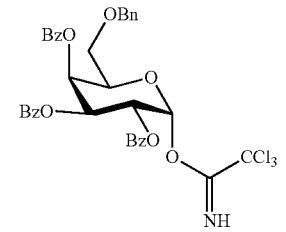

14

| Membrane Cellulose A | inert | 1000 DCM<br>1000 DCM | 70<br>70 | −12° C. to rt<br>−12° C. to rt | 1<br>1.5 | 30/SM, P<br>30/SM, P |

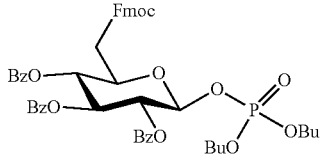

15

| Membrane Polypropylene B | inert | 1000 DCM | 75 | −12° C. to rt | 2 | 30/FC |

FC = full conversion of starting material,
SM = starting material observed,
SM, P = starting material observed/partial conversion,
NC = no conversion Different types of building blocks have been used for this approach to examine the reactivity of the different leaving groups as well as the effect of the temporary and permanent protecting groups during glycosylation. Different reaction parameters have been tested to optimize the glycosylation reaction, such as variation of solvents, different amounts of activator, and different bubbling times of the glycosylation solutions as well as different spotting methods of the desired compounds under inert and under ambient temperature (Table 3).

Figure 12:
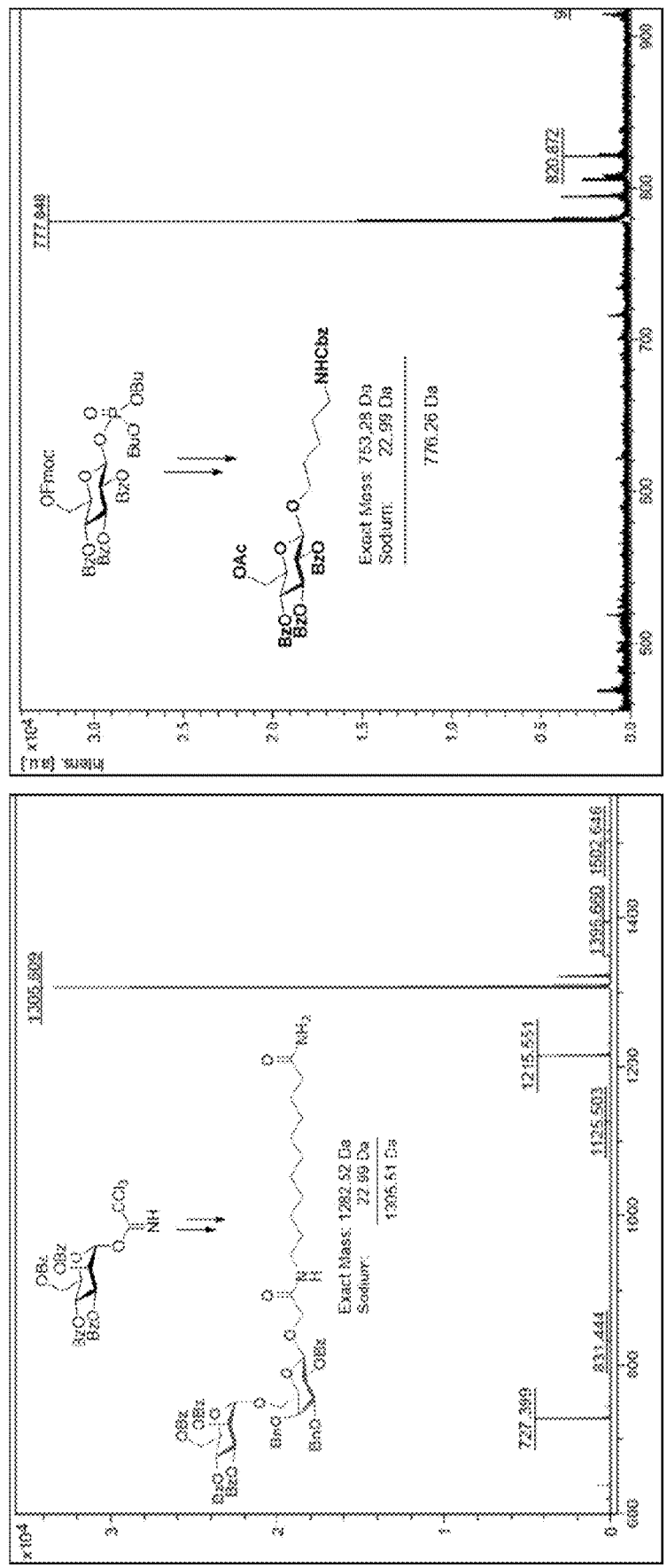
FIG. 12 shows MALDI-TOF-MS spectra after vapor-triggered glycosylation. On the left, disaccharide obtained by glycosylation of trichloroacetimidate 8 with functionalized cellulose membrane A; on the right, direct glycosylation of phosphate on functionalized polypropylene membrane B.

Suitable conditions for the vapor-triggered glycosylation on cellulose membranes with trichloroacetimidates 8, 13 and 14 and phosphate 15 have been found (see FIG. 12 for MALDI MS spectra of the products). At a constant reaction temperature below 20° C., a satisfactory deposition of the glycosylation solutions as well as the activation of the acceptor and the stereo-selective formation of the oligosaccharide was achieved.

Example 4: Glycosylation on Functionalized Cellulose Membrane

A cellulose membrane which was purchased from AIMS Scientific Products GmbH was modified to membrane 12 as described in Example 3. Two different glycosylation reactions were tested on membrane 12. The first one was performed with glycosyl imidate 8 applying the conditions shown below and the second with thioglycoside 16, conditions also shown below. Both reactions were done in solution to verify that the glycosylation reaction in general is possible on the cellulose membrane. For both reactions the glycosylation product (disaccharide) was detected via MALDI-TOF-MS after cleavage of the molecule from the membrane via UV irradiation.

Conditions for glycosylation of glycosyl imidate 8 and acceptor 12:

Glycosyl imidate 8: 25 mg
TMSOTF: 15 μl
DCM: 5 mL
NEt₃ (quenching): 300 μl
Temperature: rt
Time: 30 min

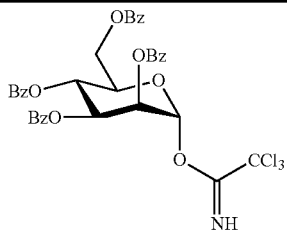

8

Conditions for glycosylation of thioglycoside 16 and acceptor 12:

Thioglycoside 16: 60.0 mg
TfOH: 1.4 μl
NIS: 35.0 mg
Dioxane: 0.333 mL
DCM: 1.66 mL
Temperature: −20° C. → 0° C.
Time: 20 min

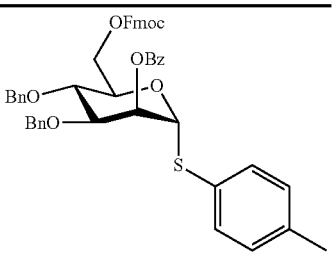

16

Figure 14:
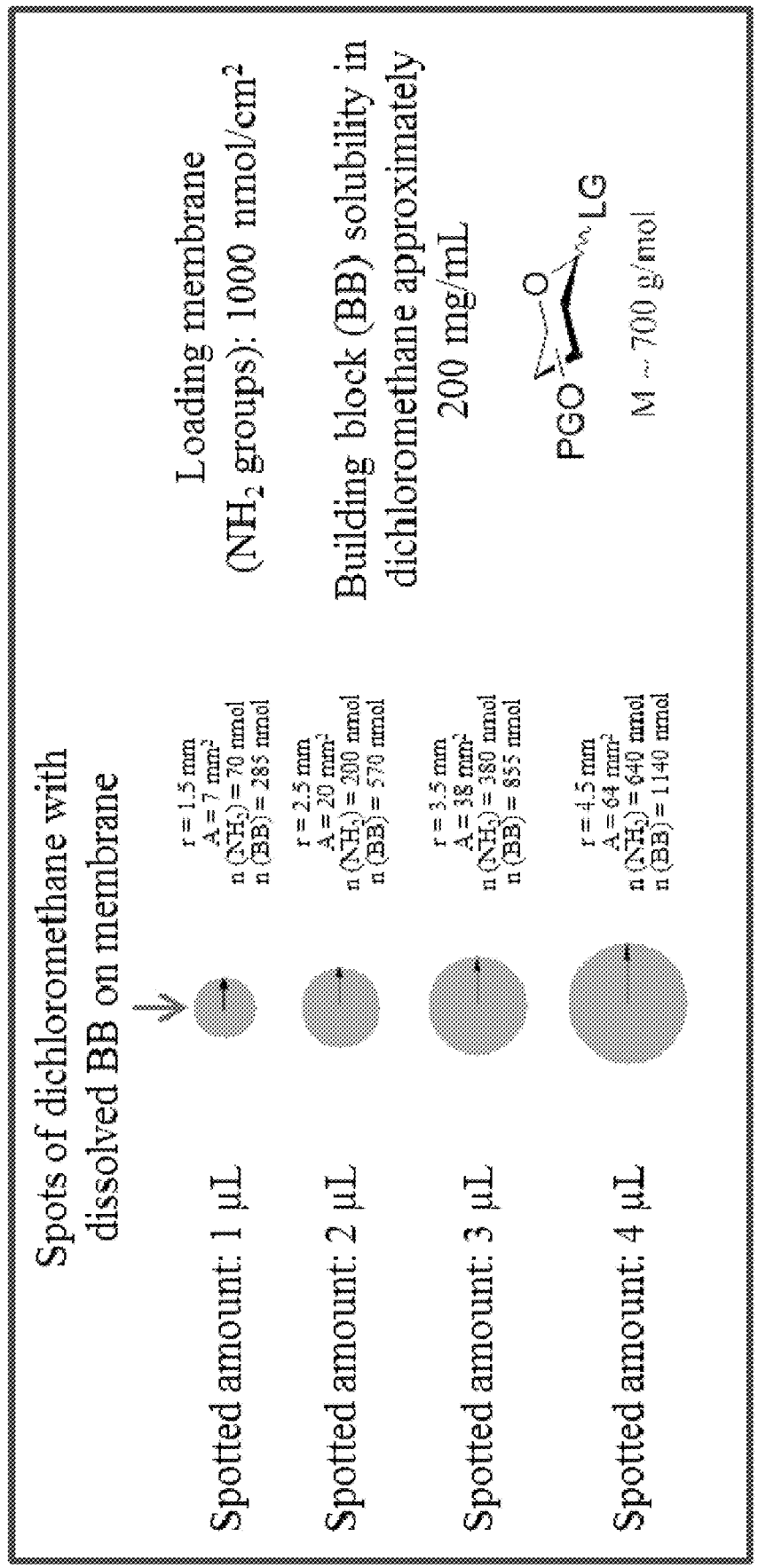
FIG. 14 Parameters for the spotting of glycosyl donor dissolved in dichloromethane. A solution of 200 mg of the building block in dichloromethane will be used. PG=protecting group, LG=leaving group. These parameters change for acetonitrile, which results in twice the radius (1 µL: r=3 mm, 2 µL: r=5 mm, 3 µL: r=7 mm, 4 µL: r=9 mm).

Example 5: Vapor-Triggered Saccharide Synthesis (Chilled Vapor Annealing Synthesis=CVAS) on Glass Slides or Membranes The herein described experiments are carried out in a reaction chamber shown in FIG. 11. The membrane or the glass slide covered with a certain pattern of glycosyl donors will be placed on the thermoelectric cooling element under inert gas atmosphere. For the patterning of the glass slides, laser induced forward transfer (cLIFT) is used as shown in FIG. 10. The patterning of the membranes will be done by using the SPOT synthesis, employing a spotting robot. The standard cellulose membrane esterified with Fmoc-β-alanine has a loading of 1000 nmol/cm². By dissolving the glycosyl donors in an aprotic organic solvent (200 mg/ml) and spotting them on these membranes, we will obtain the measured parameters shown in FIG. 14. In addition, if a supplementary reagent is required for the glycosylation reaction (e.g. N-iodosuccinimide for thioglycosides), this substance could be co-spotted on the same spots or possibly brought into vapor phase via negative pressure. For large radii of the spots the glycosyl donors must be spotted multiple times to reach a saturation of the amine groups on the membrane. After patterning the glycosyl donors on the membrane or glass slide and placing them on the thermoelectric cooling element, the reaction chamber will be evacuated and flushed with an inert gas (N₂, Ar etc.) to accomplish the glycosylation reactions avoiding moisture or air. Additionally, to get rid of traces of water and other volatile compounds adsorbed by the solid support (membrane or glass slide), the thermoelectric cooling element should be able to warm the surface up to +150° C. to remove these compounds under vacuum.

For the CVAS process itself, the following parameters are used:
Solvents:
  DCM, toluene, acetonitrile, ethers (1,4-dioxane, diethyl ether, MTBE)
Gas-/Vapor Phase:
  Inert gas (N2, Ar.)
Parameter:
Vapor
  Laminar gas flow
  0-2000 sccm/min (0-2 L/min) flow rate
  0-100% vapor saturation/composition
Temperature
  $T_{gas}$=RT gas/vapor
  Vapor preparation:
    $T_{bottle1}$ First 10-100 ml bottle (RT+$\Delta T_{bottle1}$)~40° C.
    $T_{bottle2}$ Second 10-100 ml bottle~RT
  $T_{sampleholder}$ sample holder−50° C.-+150° C., with $\Delta T_{sampleholder}$>=0° C.
Vapor chamber:
  Volume vapor chamber $V_{chamber}$~100-500 ml
  Atmospheric pressure for process, $\Delta p \geq 0$ Pa
  Vacuum for $H_2O$ removal (typical vacuum pump limits $10^{-2}$-$10^{-3}$ bar)
Process time (glycosylation time)
  $t_{process}$~1 min-12 h
  Sequential vapor exchange (gas vs. solvent/reagent vapor)
Vapor Preparation:

In the setup (FIG. 11), the first bottle is heated to RT+ΔT to saturate the vapor. The second bottle is kept at RT, which results in 100% saturated vapor.

Condensation on the substrate: The speed of vapor condensation on the sample surface is adjusted by the temperature difference ΔT (is |$T_{sampleholder}$-$T_{gas}$|). Condensation occurs at ΔT=0 (vapor vs. sample), when the vapor saturation is 100% or when ΔT>0, the vapor condensates with saturation<100%. The reaction time is between 10 minutes up to one hour.

After the reaction is finished, the reactive support is quenched by adding a base (e.g. piperidine, triethylamine) within the reaction chamber. Then the substrate is removed of the chamber and washed. After the deprotection of a temporary protecting on the sugar moiety the substrate is used in the next CVAS glycosylation reaction.

Example 6: Parallel Vapor-Triggered Glycosylation on Membranes

Figure 11:
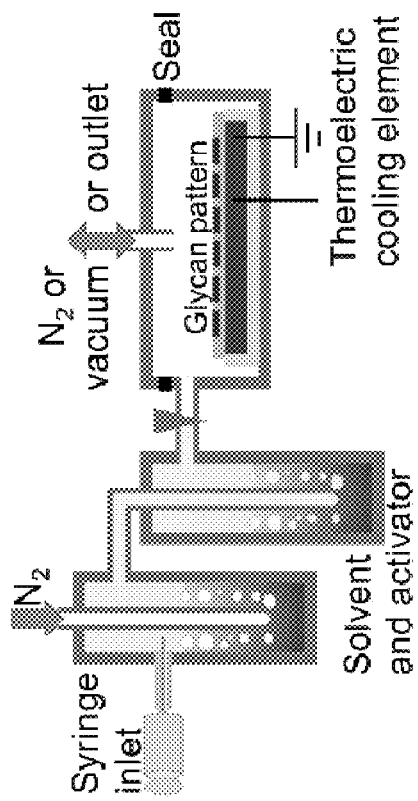
FIG. 11 shows an alternative setup of a vapor annealing coupling chamber.
Figure 15:
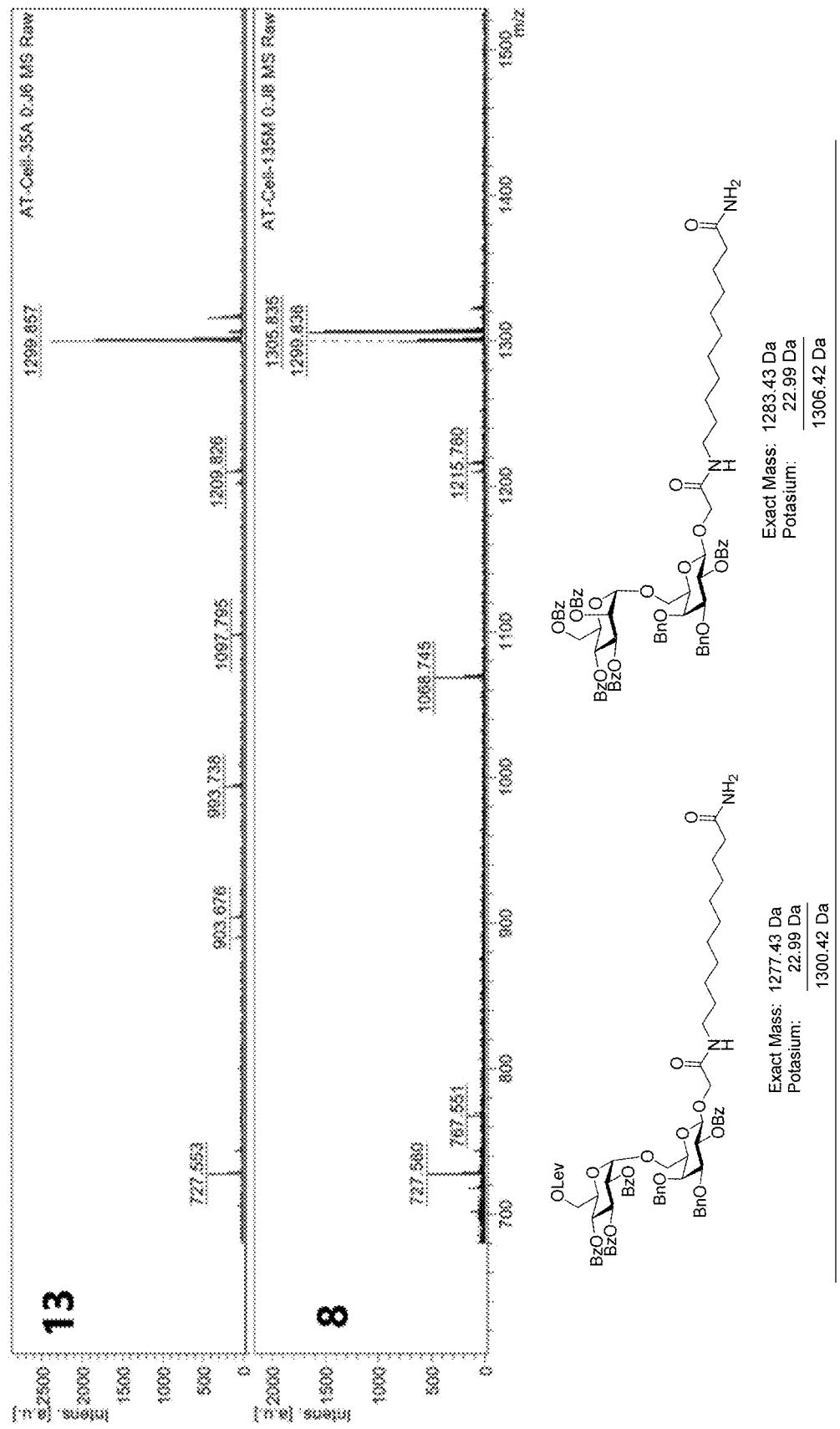
FIG. 15 shows MALDI-TOF MS spectra: upper spectrum corresponds to the membrane area where only the glucose donor 13 was spotted; lower spectrum: corresponds to the membrane area where only the mannose donor 8 was spotted.

Two different acetimidates glucose 13 and mannose 8 were spotted onto the same membrane 12A (see Example 3) on different areas A (13) and B (8) under inert conditions and placed inside the chamber for glycosylation (FIG. 11). The glycosylation was performed with a glycosylation solution of 80 μL TMSOTf in 1000 μL DCM. Inert gas was passed through the glycosylation solution for 2 minutes and the membrane was left in the vapor for 30 minutes reaction time. The reaction temperature was −12° C. After the completion of the reaction, and the UV-cleavage, the MALDI-TOF showed that the desired sequences were formed (FIG. 15).

What is claimed is:

1. A method for synthesizing saccharide comprising the steps:
   A) providing a solid support with at least one immobilized acceptor group for reacting with a saccharide;
   B) delivering the saccharide onto the solid support;
   C) applying a vapor of a mixture of a glycosylation reagent and a solvent onto the solid support at a temperature below 20° C. in order to initiate a coupling reaction of the saccharide to the at least one immobilized acceptor group.

2. The method according to claim 1, wherein step C) is carried out at a temperature below 5° C.

3. The method according to claim 1, wherein the ratio of the solvent and the glycosylation reagent is in the range of 1:10 to 100,000:1.

4. The method according to claim 1, wherein the solvent is an aprotic organic solvent selected from: methylene chloride, chloroform, acetonitrile, diethyl ether, 1,4-dioxane, methyl tert-butyl ether, toluene and ethyl acetate.

5. The method according to claim 1, wherein the glycosylation reagent is a Lewis acid selected from: AgOTf, $BF_3 \cdot OEt_2$, trimethylsilyl trifluoromethanesulfonate, trifluoromethanesulfonic acid, trifluoromethanesulfonic anhydride, lanthanoid(III) triflates, NIS/AgOTf, NIS/TfOH or dimethyl(methylthio)sulfonium trifluoromethanesulfonate.

6. The method according to claim 1, wherein the saccharide is a protected glycosyl donor comprising a glycal, epoxide or orthoester group or having a leaving group at the reducing end selected from halogen, —O—C(=NH)—$CCl_3$, —O—C(=NPh)—$CF_3$, —OAc, —$SR^5$, —SO-Ph, —$SO_2$-Ph, —O—$(CH_2)_3$—CH=$CH_2$, —O—$P(OR^5)_2$, —O—$PO(OR^5)_2$, —O—CO—$OR^5$, —O—CO—$SR^5$, —O—CS—$SR^5$, —O—CS—$OR^5$,

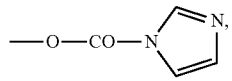

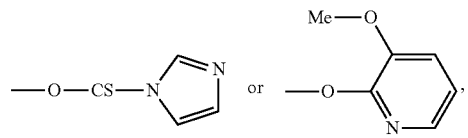

wherein $R^5$ represents an alkyl or aryl group.

7. The method according to claim 1, wherein in step B) the saccharide is a monosaccharide.

8. The method according to claim 1, further comprising step C') between step B) and step C):
   C') drying the solid support obtained in step B) under reduced pressure and/or heating.

9. The method according to claim 1, further comprising step K)
   K) performing removal of protecting groups from the saccharide obtained in step C).

10. The method according to claim 1, wherein the at least one immobilized acceptor group for reacting with the saccharide is located at discrete locations forming an array on the solid support.

11. The method according to claim 1, further comprising steps L) and M)
    L) cleaving the saccharide from the solid support; and
    M) optionally purifying the saccharide obtained from step L).

12. A method of detecting antibodies or glycan-binding proteins in a test sample comprising contacting the test sample with a saccharide array obtained by the method of claim 10 and observing whether one or more saccharides are bound by an antibody or glycan-binding protein in the test sample.

13. A saccharide synthesizer comprising:
   a substrate, the substrate having a surface and being configured to support a solid support with at least one immobilized acceptor group for reacting with a saccharide;
   means for delivering a saccharide to a solid support with at least one immobilized acceptor group for reacting with a saccharide supported by the substrate;
   a chamber comprising
   a process space;
   a vapor supply in fluid communication with the process space, the vapor supply configured to supply a vapor comprising a solvent and a glycosylation reagent to the process space;
   a cooling element positioned within the processing chamber configured to cool the solid support by heat transfer through the substrate;
   an exhaust port in the processing chamber configured in fluid communication with an isolation valve;
   a purge gas supply in fluid communication with the process space, the purge gas supply configured to supply a purge gas to the process space effective to displace the vapor from the process space,
   wherein the substrate is positioned in the process space of the chamber.

14. The synthesizer according to claim 13, wherein the means for delivering a saccharide to a solid support comprises a capillary needle which is in fluid connection with a reservoir containing a saccharide, optionally a syringe connected to said capillary needle or optionally a microactuator connected to said capillary needle; or a laser for transferring the saccharide in a polymer matrix onto the solid support.

15. The synthesizer according to claim 13, wherein the cooling element of the chamber cools the solid support below a temperature of 5° C.

* * * * *